US005605690A

United States Patent [19]
Jacobs et al.

[11] Patent Number: 5,605,690
[45] Date of Patent: Feb. 25, 1997

[54] METHODS OF LOWERING ACTIVE TNF-α LEVELS IN MAMMALS USING TUMOR NECROSIS FACTOR RECEPTOR

[75] Inventors: Cindy A. Jacobs; Craig A. Smith, both of Seattle, Wash.

[73] Assignee: Immunex Corporation, Seattle, Wash.

[21] Appl. No.: 385,229

[22] Filed: Feb. 8, 1995

Related U.S. Application Data

[63] Continuation of Ser. No. 946,236, Sep. 15, 1992, abandoned, which is a continuation-in-part of Ser. No. 523,635, May 10, 1990, Pat. No. 5,395,760, which is a continuation-in-part of Ser. No. 421,417, Oct. 13, 1989, abandoned, which is a continuation-in-part of Ser. No. 405,370, Sep. 11, 1989, abandoned, which is a continuation-in-part of Ser. No. 403,241, Sep. 5, 1989, abandoned.

[51] Int. Cl.$^6$ .................. A61K 39/395; A61K 38/00; C12P 21/04; C07K 14/715
[52] U.S. Cl. .................. 424/134.1; 435/69.7; 514/12; 514/825; 530/350; 530/387.3; 530/866; 530/868
[58] Field of Search .................. 435/69.1, 69.7, 435/172.3, 240.27; 424/85.1, 134.1; 530/351, 387.3, 868; 935/9, 12, 15

[56] References Cited

U.S. PATENT DOCUMENTS

| | | | |
|---|---|---|---|
| 4,675,285 | 6/1987 | Clark et al. | 435/6 |
| 4,770,995 | 9/1988 | Rubin et al. | 436/544 |
| 5,116,964 | 5/1992 | Capon et al. | 536/27 |
| 5,512,544 | 4/1996 | Wallach et al. | |

FOREIGN PATENT DOCUMENTS

| | | | |
|---|---|---|---|
| 0308378 | 6/1989 | European Pat. Off. | C12N 15/00 |
| 0422339 | 7/1990 | European Pat. Off. | C12N 15/12 |
| 61-293924 | 12/1986 | Japan | A61K 37/02 |
| 0334165 | 9/1989 | Switzerland | C12P 21/00 |
| 2218101 | 11/1989 | United Kingdom | C07K 15/14 |
| WO9013575 | 11/1990 | WIPO | C07K 15/14 |

OTHER PUBLICATIONS

Beutler of *Tumor Necrosis Factors* . . . , Raven Press, 1185 Ave of the Americas, NY, NY, 10036.
Steiner, Biotechnology 12: 1313, Dec. 1994.
"US News & World Report", p. 13, Aug. 1, 1994.
*Immunophysiology* pp, 234–235, 1990, Oppenheim.
Pavillo–New Eng J of Med., "Mech. of Disease, Pathogenetic Mech. of Septic Shock", pp. 1471–1477, 1993.
Hoogenboom et al, Molecular Immunology 28(9):1027–1037 1991, "Construction & Expression of Ab–TNF fusion proteins".
Harris, The New England Journal of Med., 322(18): 1277–1289 (1990) "Mechanisms of Disease: Rheumatoid Arthritis".
Brennan et al, The Lancet, Jul. 29, 1993, 244–247 "Inhib. Effect of TNF–α Ab on Synovial Cell IL–1 Production in Rh. Arthritis".

Smith et al, Science, 248: 1019–1023, 1990 "A Receptor for TNF defines an Unusual Family of Cellular & Viral Proteins".
Bloom, J. Clin. Invest., 91: 1265–1266 (1993) "The Power of Negative Thinking".
Pennica et al., "Human tumour necrosis factor: precursor structure, expression and homology to lymphotoxin," *Nature* 312: 724 (1984).
Gray et al., "Cloning and expression of cDNA for human lymphotoxin, a lymphokine with tumour necrosis activity," *Nature* 312: 721 (1984).
Baglioni et al., "Binding of Human Tumor Necrosis Factor to High Affinity Receptors on HeLa and Lymphoblastoid Cells Sensitive to Growth Inhibition," *J. Biol. Chem.* 260:13395 (1985).
Aggarwall et al., "Characterization of receptors for human tumour necrosis factor and their regulation by γ–interferon," *Nature* 318:665 (1985).
Yoshie et al., "Binding and Crosslinking of $^{125}$I–Labeled Recombinant Human Tumor Necrosis Factor to Cell Surface Receptors," *J. Biochem.* 100:531 (1986).
Israel et al., "Binding of Human TNF–α to High–Affinity Cell Surface Receptors: Effect of IFN," *Immunology Letters* 12:217 (1986).
Creasley et al., "A high molecular weight component of the human tumor necrosis factor receptor is associated with cytotoxicity," *Proc. Natl. Acad. Sci. USA* 84:3293 (1987).
Stauber et al., "Human Tumor Necrosis Factor–α Receptor," *J. Biol. Chem.* 263:19098 (1988).
Aggarwal and Eessalu, "Induction of Receptors for Tumor Necrosis Factor–α by Interferons Is Not a Major Mechanism for Their Synergistic Cytotoxic Response," *J. Biol. Chem.* 263:10000 (1987).
Tsujimoto et al., "Interferon–γ Enhances Expression of Cellular Receptors for Tumor Necrosis Factor," *J. Immun.* 136:2441 (1987).
Holtmann and Wallach, "Down Regulation of the Receptors for Tumor Necrosis Factor by Interleukin 1 and 4β–Phorbol–12–Myristate–13–Acetate," *J. Immonol.* 139:1161 (1987).
Shalaby et al., "Receptor Binding and Activation of Polymorphonuclear Neutrophils by Tumor Necrosis Factor–Alpha," *J. Leukocyte Biol.* 41:196 (1987).
Unglaub et al, "Downregulation of Tumor Necrosis Factor (TNF) Sensitivity Via Modulation of TNF Binding Capacity by Protein Kinase C Activators," *J. Exp. Med.* 166:1788 (1987).
Yonehara et al., "A Cell–Killing Monoclonal Antibody (ANTI–Fas) to a Cell Surface Antigen Co–Downregulated with the Receptor of Tumor Necrosis Factor," *J. Exp. Med.* 167:1511 (1988).

(List continued on next page.)

*Primary Examiner*—Lila Feisee
*Assistant Examiner*—John Lucas
*Attorney, Agent, or Firm*—Stephen L. Malaska

[57] ABSTRACT

A method for treating TNF–dependent inflammatory diseases in a mammal by administering a TNF antagonist, such as soluble TNFR.

6 Claims, 7 Drawing Sheets

OTHER PUBLICATIONS

Peetre et al., "A tumor necrosis factor binding protein is present in human biological fluids," *Eur. J. Haematol.* 41:414 (1988).

Seckinger et al., "A Human Inhibitor of Tumor Necrosis Factor α," *J. Exp. Med.* 167:1511 (1988).

Seckinger et al., "Purification and Biologic Characterization of a Specific Tumor Necrosis Factor α Inhibitor," *J. Biol. Chem.* 264:11966 (1989).

Engelmann et al., "A Tumor Necrosis Factor–binding Protein Purified to Homogeneity from Human Urine Protects Cells from Tumor Necrosis Factor Toxicity," *J. Biol. Chem.* 264:11974 (1989).

Okayama and Berg, "High–Efficiency Cloning of Full–Length cDNA," *Mol. Cell. Biol.* 2:161 (1982).

Okayama and Berg, "A cDNA Cloning Vector That Permits Expression of cDNA Inserts in Mammalian Cells," *Mol. Cell. Biol.* 3:280 (1983).

Aruffo and Seed, "Molecular cloning of a CD28 cDNA by a high–efficiency COS cell expression system," *Proc. Natl. Acad. Sci. USA* 84:8573 (1987).

Yamasaki et al., "Cloning and Expression of the Human Interleukin-6 (BSF–2/IFNβ 2) Receptor," *Science* 241:825 (1988).

Sims et al., "cDNA Expression Cloning of the IL–1 Receptor, a Member of the Immunoglobulin Superfamily," *Science* 241:585 (1988).

Tsujimoto et al., Arch. Biochem. and Biophys., "Characterization and Affinity Crosslinking of Receptors for Tumor Necrosis" 563–568 (1986).

Suggs et al., "Use of synthetic oligonucleotides as hybridization probes", *PNAS* 78:6613–6617 (1981).

Kull et al., "Cellular receptor for $^{125}$I–labelled tumor necrosis factor . . .", *PNAS* 82:5756–5760 (1985).

Smith et al., "A receptor for tumor necrosis factor defines and unusual family of cellular and viral proteins", *Science* 248:1019–1023 (1990).

Meller et al., "Complementary DNA cloning of a receptor for tumor necrosis factor and demonstration of a shed form of the receptor" *Proc. Natl. Acad. Sci. U.S.*, 87:6151–6155 (1990).

Loetscher et al., "Molecular cloning and expression of the human 55 kd tumor necrosis factor receptor" *Cell* 61:351–359 (1990).

Schall et al., "Molecular cloning and expression of a receptor for human tumor necrosis factor" *Cell* 61:361–370 (1990).

Engelmann et al., "Two tumor necrosis factor–binding proteins purified from human urine" *J. Biol. Chem.* 265:1531–1536.

Smith et al., "Blocking of HIV–1 Infectivity by a Soluble, Secreted Form of the CD4 Antigen", *Science* 238:1704–1707.

□ BHK-TNFR:Fc, 5μg / joint
■ TNFR monomer, 5μg / joint
● mu IL-1R, 1μg / joint
▲ TNFR monomer/IL-1R, 10μg/1μg/joint
○ Diluent

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 1641 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
      ( A ) ORGANISM: Homo sapiens
      ( G ) CELL TYPE: Fibroblast
      ( H ) CELL LINE: WI-26 VA4

(vii) IMMEDIATE SOURCE:
(A) LIBRARY: WI-26 VA4
(B) CLONE: Clone 1

(ix) FEATURE:
(A) NAME/KEY: CDS
(B) LOCATION: 88..1473

(ix) FEATURE:
(A) NAME/KEY: mat_peptide
(B) LOCATION: 154..1470

(ix) FEATURE:
(A) NAME/KEY: sig_peptide
(B) LOCATION: 88..153

(xi) SEQUENCE DESCRIPTION: SEQ ID NO:1:

```
GCGAGGCAGG CAGCCTGGAG AGAAGGCGCT GGGCTGCGAG GGCGCGAGGG CGCGAGGGCA        60

GGGGGCAACC GGACCCCGCC CGCATCC ATG GCG CCC GTC GCC GTC TGG GCC           111
                                Met Ala Pro Val Ala Val Trp Ala
                                -22         -20                 -15

GCG CTG GCC GTC GGA CTG GAG CTC TGG GCT GCG GCG CAC GCC TTG CCC         159
Ala Leu Ala Val Gly Leu Glu Leu Trp Ala Ala Ala His Ala Leu Pro
            -10                 -5                              1

GCC CAG GTG GCA TTT ACA CCC TAC GCC CCG GAG CCC GGG AGC ACA TGC         207
Ala Gln Val Ala Phe Thr Pro Tyr Ala Pro Glu Pro Gly Ser Thr Cys
        5                   10                  15

CGG CTC AGA GAA TAC TAT GAC CAG ACA GCT CAG ATG TGC TGC AGC AAA         255
Arg Leu Arg Glu Tyr Tyr Asp Gln Thr Ala Gln Met Cys Cys Ser Lys
        20                  25                  30

TGC TCG CCG GGC CAA CAT GCA AAA GTC TTC TGT ACC AAG ACC TCG GAC         303
Cys Ser Pro Gly Gln His Ala Lys Val Phe Cys Thr Lys Thr Ser Asp
35                  40                  45                  50

ACC GTG TGT GAC TCC TGT GAG GAC AGC ACA TAC ACC CAG CTC TGG AAC         351
Thr Val Cys Asp Ser Cys Glu Asp Ser Thr Tyr Thr Gln Leu Trp Asn
                55                  60                  65

TGG GTT CCC GAG TGC TTG AGC TGT GGC TCC CGC TGT AGC TCT GAC CAG         399
Trp Val Pro Glu Cys Leu Ser Cys Gly Ser Arg Cys Ser Ser Asp Gln
            70                  75                  80

GTG GAA ACT CAA GCC TGC ACT CGG GAA CAG AAC CGC ATC TGC ACC TGC         447
Val Glu Thr Gln Ala Cys Thr Arg Glu Gln Asn Arg Ile Cys Thr Cys
        85                  90                  95

AGG CCC GGC TGG TAC TGC GCG CTG AGC AAG CAG GAG GGG TGC CGG CTG         495
Arg Pro Gly Trp Tyr Cys Ala Leu Ser Lys Gln Glu Gly Cys Arg Leu
100                 105                 110

TGC GCG CCG CTG CGC AAG TGC CGC CCG GGC TTC GGC GTG GCC AGA CCA         543
Cys Ala Pro Leu Arg Lys Cys Arg Pro Gly Phe Gly Val Ala Arg Pro
115                 120                 125                 130

GGA ACT GAA ACA TCA GAC GTG GTG TGC AAG CCC TGT GCC CCG GGG ACG         591
Gly Thr Glu Thr Ser Asp Val Val Cys Lys Pro Cys Ala Pro Gly Thr
                135                 140                 145

TTC TCC AAC ACG ACT TCA TCC ACG GAT ATT TGC AGG CCC CAC CAG ATC         639
Phe Ser Asn Thr Thr Ser Ser Thr Asp Ile Cys Arg Pro His Gln Ile
            150                 155                 160

TGT AAC GTG GTG GCC ATC CCT GGG AAT GCA AGC ATG GAT GCA GTC TGC         687
Cys Asn Val Val Ala Ile Pro Gly Asn Ala Ser Met Asp Ala Val Cys
        165                 170                 175

ACG TCC ACG TCC CCC ACC CGG AGT ATG GCC CCA GGG GCA GTA CAC TTA         735
Thr Ser Thr Ser Pro Thr Arg Ser Met Ala Pro Gly Ala Val His Leu
180                 185                 190

CCC CAG CCA GTG TCC ACA CGA TCC CAA CAC ACG CAG CCA ACT CCA GAA         783
Pro Gln Pro Val Ser Thr Arg Ser Gln His Thr Gln Pro Thr Pro Glu
195                 200                 205                 210
```

```
CCC AGC ACT GCT CCA AGC ACC TCC TTC CTG CTC CCA ATG GGC CCC AGC      831
Pro Ser Thr Ala Pro Ser Thr Ser Phe Leu Leu Pro Met Gly Pro Ser
            215                 220                 225

CCC CCA GCT GAA GGG AGC ACT GGC GAC TTC GCT CTT CCA GTT GGA CTG      879
Pro Pro Ala Glu Gly Ser Thr Gly Asp Phe Ala Leu Pro Val Gly Leu
            230                 235                 240

ATT GTG GGT GTG ACA GCC TTG GGT CTA CTA ATA ATA GGA GTG GTG AAC      927
Ile Val Gly Val Thr Ala Leu Gly Leu Leu Ile Ile Gly Val Val Asn
            245                 250                 255

TGT GTC ATC ATG ACC CAG GTG AAA AAG AAG CCC TTG TGC CTG CAG AGA      975
Cys Val Ile Met Thr Gln Val Lys Lys Lys Pro Leu Cys Leu Gln Arg
            260                 265                 270

GAA GCC AAG GTG CCT CAC TTG CCT GCC GAT AAG GCC CGG GGT ACA CAG     1023
Glu Ala Lys Val Pro His Leu Pro Ala Asp Lys Ala Arg Gly Thr Gln
275                 280                 285                 290

GGC CCC GAG CAG CAG CAC CTG CTG ATC ACA GCG CCG AGC TCC AGC AGC     1071
Gly Pro Glu Gln Gln His Leu Leu Ile Thr Ala Pro Ser Ser Ser Ser
            295                 300                 305

AGC TCC CTG GAG AGC TCG GCC AGT GCG TTG GAC AGA AGG GCG CCC ACT     1119
Ser Ser Leu Glu Ser Ser Ala Ser Ala Leu Asp Arg Arg Ala Pro Thr
            310                 315                 320

CGG AAC CAG CCA CAG GCA CCA GGC GTG GAG GCC AGT GGG GCC GGG GAG     1167
Arg Asn Gln Pro Gln Ala Pro Gly Val Glu Ala Ser Gly Ala Gly Glu
            325                 330                 335

GCC CGG GCC AGC ACC GGG AGC TCA GAT TCT TCC CCT GGT GGC CAT GGG     1215
Ala Arg Ala Ser Thr Gly Ser Ser Asp Ser Ser Pro Gly Gly His Gly
            340                 345                 350

ACC CAG GTC AAT GTC ACC TGC ATC GTG AAC GTC TGT AGC AGC TCT GAC     1263
Thr Gln Val Asn Val Thr Cys Ile Val Asn Val Cys Ser Ser Ser Asp
355                 360                 365                 370

CAC AGC TCA CAG TGC TCC TCC CAA GCC AGC TCC ACA ATG GGA GAC ACA     1311
His Ser Ser Gln Cys Ser Ser Gln Ala Ser Ser Thr Met Gly Asp Thr
            375                 380                 385

GAT TCC AGC CCC TCG GAG TCC CCG AAG GAC GAG CAG GTC CCC TTC TCC     1359
Asp Ser Ser Pro Ser Glu Ser Pro Lys Asp Glu Gln Val Pro Phe Ser
            390                 395                 400

AAG GAG GAA TGT GCC TTT CGG TCA CAG CTG GAG ACG CCA GAG ACC CTG     1407
Lys Glu Glu Cys Ala Phe Arg Ser Gln Leu Glu Thr Pro Glu Thr Leu
            405                 410                 415

CTG GGG AGC ACC GAA GAG AAG CCC CTG CCC CTT GGA GTG CCT GAT GCT     1455
Leu Gly Ser Thr Glu Glu Lys Pro Leu Pro Leu Gly Val Pro Asp Ala
            420                 425                 430

GGG ATG AAG CCC AGT TAACCAGGCC GGTGTGGGCT GTGTCGTAGC CAAGGTGGGC     1510
Gly Met Lys Pro Ser
435                 440

TGAGCCCTGG CAGGATGACC CTGCGAAGGG GCCCTGGTCC TTCCAGGCCC CCACCACTAG   1570

GACTCTGAGG CTCTTTCTGG GCCAAGTTCC TCTAGTGCCC TCCACAGCCG CAGCCTCCCT   1630

CTGACCTGCA G                                                        1641
```

( 2 ) INFORMATION FOR SEQ ID NO:2:

( i ) SEQUENCE CHARACTERISTICS:
            ( A ) LENGTH: 461 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

```
Met Ala Pro Val Ala Val Trp Ala Ala Leu Ala Val Gly Leu Glu Leu
```

|       | -22 |     | -20 |     |     | -15 |     |     |     | -10 |     |     |     |
|-------|-----|-----|-----|-----|-----|-----|-----|-----|-----|-----|-----|-----|-----|
| Trp   | Ala | Ala | Ala | His | Ala | Leu | Pro | Ala | Gln | Val | Ala | Phe | Thr | Pro | Tyr |
|       | -5  |     |     |     |     | 1   |     |     |     | 5   |     |     |     |     | 10  |
| Ala   | Pro | Glu | Pro | Gly | Ser | Thr | Cys | Arg | Leu | Arg | Glu | Tyr | Tyr | Asp | Gln |
|       |     |     |     | 15  |     |     |     |     | 20  |     |     |     |     | 25  |     |
| Thr   | Ala | Gln | Met | Cys | Cys | Ser | Lys | Cys | Ser | Pro | Gly | Gln | His | Ala | Lys |
|       |     |     | 30  |     |     |     | 35  |     |     |     |     | 40  |     |     |     |
| Val   | Phe | Cys | Thr | Lys | Thr | Ser | Asp | Thr | Val | Cys | Asp | Ser | Cys | Glu | Asp |
|       |     | 45  |     |     |     | 50  |     |     |     |     | 55  |     |     |     |     |
| Ser   | Thr | Tyr | Thr | Gln | Leu | Trp | Asn | Trp | Val | Pro | Glu | Cys | Leu | Ser | Cys |
|       | 60  |     |     |     |     | 65  |     |     |     | 70  |     |     |     |     |     |
| Gly   | Ser | Arg | Cys | Ser | Ser | Asp | Gln | Val | Glu | Thr | Gln | Ala | Cys | Thr | Arg |
| 75    |     |     |     |     | 80  |     |     |     |     | 85  |     |     |     |     | 90  |
| Glu   | Gln | Asn | Arg | Ile | Cys | Thr | Cys | Arg | Pro | Gly | Trp | Tyr | Cys | Ala | Leu |
|       |     |     |     | 95  |     |     |     |     | 100 |     |     |     |     | 105 |     |
| Ser   | Lys | Gln | Glu | Gly | Cys | Arg | Leu | Cys | Ala | Pro | Leu | Arg | Lys | Cys | Arg |
|       |     |     | 110 |     |     |     |     | 115 |     |     |     |     | 120 |     |     |
| Pro   | Gly | Phe | Gly | Val | Ala | Arg | Pro | Gly | Thr | Glu | Thr | Ser | Asp | Val | Val |
|       |     | 125 |     |     |     |     | 130 |     |     |     |     | 135 |     |     |     |
| Cys   | Lys | Pro | Cys | Ala | Pro | Gly | Thr | Phe | Ser | Asn | Thr | Thr | Ser | Ser | Thr |
|       | 140 |     |     |     |     | 145 |     |     |     |     | 150 |     |     |     |     |
| Asp   | Ile | Cys | Arg | Pro | His | Gln | Ile | Cys | Asn | Val | Val | Ala | Ile | Pro | Gly |
| 155   |     |     |     |     | 160 |     |     |     |     | 165 |     |     |     |     | 170 |
| Asn   | Ala | Ser | Met | Asp | Ala | Val | Cys | Thr | Ser | Thr | Ser | Pro | Thr | Arg | Ser |
|       |     |     | 175 |     |     |     |     | 180 |     |     |     |     | 185 |     |     |
| Met   | Ala | Pro | Gly | Ala | Val | His | Leu | Pro | Gln | Pro | Val | Ser | Thr | Arg | Ser |
|       |     |     | 190 |     |     |     |     | 195 |     |     |     |     | 200 |     |     |
| Gln   | His | Thr | Gln | Pro | Thr | Pro | Glu | Pro | Ser | Thr | Ala | Pro | Ser | Thr | Ser |
|       |     | 205 |     |     |     |     | 210 |     |     |     |     | 215 |     |     |     |
| Phe   | Leu | Leu | Pro | Met | Gly | Pro | Ser | Pro | Pro | Ala | Glu | Gly | Ser | Thr | Gly |
|       | 220 |     |     |     |     | 225 |     |     |     |     | 230 |     |     |     |     |
| Asp   | Phe | Ala | Leu | Pro | Val | Gly | Leu | Ile | Val | Gly | Val | Thr | Ala | Leu | Gly |
| 235   |     |     |     |     | 240 |     |     |     |     | 245 |     |     |     |     | 250 |
| Leu   | Leu | Ile | Ile | Gly | Val | Val | Asn | Cys | Val | Ile | Met | Thr | Gln | Val | Lys |
|       |     |     |     | 255 |     |     |     |     | 260 |     |     |     |     | 265 |     |
| Lys   | Lys | Pro | Leu | Cys | Leu | Gln | Arg | Glu | Ala | Lys | Val | Pro | His | Leu | Pro |
|       |     |     | 270 |     |     |     |     | 275 |     |     |     |     | 280 |     |     |
| Ala   | Asp | Lys | Ala | Arg | Gly | Thr | Gln | Gly | Pro | Glu | Gln | Gln | His | Leu | Leu |
|       |     | 285 |     |     |     |     | 290 |     |     |     |     | 295 |     |     |     |
| Ile   | Thr | Ala | Pro | Ser | Ser | Ser | Ser | Ser | Ser | Leu | Glu | Ser | Ser | Ala | Ser |
|       | 300 |     |     |     |     | 305 |     |     |     |     | 310 |     |     |     |     |
| Ala   | Leu | Asp | Arg | Arg | Ala | Pro | Thr | Arg | Asn | Gln | Pro | Gln | Ala | Pro | Gly |
| 315   |     |     |     |     | 320 |     |     |     |     | 325 |     |     |     |     | 330 |
| Val   | Glu | Ala | Ser | Gly | Ala | Gly | Glu | Ala | Arg | Ala | Ser | Thr | Gly | Ser | Ser |
|       |     |     |     | 335 |     |     |     |     | 340 |     |     |     |     | 345 |     |
| Asp   | Ser | Ser | Pro | Gly | Gly | His | Gly | Thr | Gln | Val | Asn | Val | Thr | Cys | Ile |
|       |     |     | 350 |     |     |     |     | 355 |     |     |     |     | 360 |     |     |
| Val   | Asn | Val | Cys | Ser | Ser | Ser | Asp | His | Ser | Ser | Gln | Cys | Ser | Ser | Gln |
|       |     | 365 |     |     |     |     | 370 |     |     |     |     | 375 |     |     |     |
| Ala   | Ser | Ser | Thr | Met | Gly | Asp | Thr | Asp | Ser | Ser | Pro | Ser | Glu | Ser | Pro |
|       |     | 380 |     |     |     |     | 385 |     |     |     |     | 390 |     |     |     |
| Lys   | Asp | Glu | Gln | Val | Pro | Phe | Ser | Lys | Glu | Glu | Cys | Ala | Phe | Arg | Ser |
| 395   |     |     |     |     | 400 |     |     |     |     | 405 |     |     |     |     | 410 |

```
Gln  Leu  Glu  Thr  Pro  Glu  Thr  Leu  Leu  Gly  Ser  Thr  Glu  Glu  Lys  Pro
                    415                      420                     425

Leu  Pro  Leu  Gly  Val  Pro  Asp  Ala  Gly  Met  Lys  Pro  Ser
               430                      435
```

( 2 ) INFORMATION FOR SEQ ID NO:3:

( i ) SEQUENCE CHARACTERISTICS:
        ( A ) LENGTH: 1557 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
        ( B ) CLONE: TNFR/Fc Fusion Protein ( i x ) FEATURE:
        ( A ) NAME/KEY: CDS
        ( B ) LOCATION: 1..1557

( i x ) FEATURE:
        ( A ) NAME/KEY: mat_peptide
        ( B ) LOCATION: 1..1554

( x i ) SEQUENCE DESCRIPTION: SEQ ID NO:3:

```
GCG  AGG  CAG  GCA  GCC  TGG  AGA  GAA  GGC  GCT  GGG  CTG  CGA  GGG  CGC  GAG      48
Ala  Arg  Gln  Ala  Ala  Trp  Arg  Glu  Gly  Ala  Gly  Leu  Arg  Gly  Arg  Glu
 1              5                        10                       15

GGC  GCG  AGG  GCA  GGG  GGC  AAC  CGG  ACC  CCG  CCC  GCA  TCC  ATG  GCG  CCC      96
Gly  Ala  Arg  Ala  Gly  Gly  Asn  Arg  Thr  Pro  Pro  Ala  Ser  Met  Ala  Pro
               20                        25                       30

GTC  GCC  GTC  TGG  GCC  GCG  CTG  GCC  GTC  GGA  CTG  GAG  CTC  TGG  GCT  GCG     144
Val  Ala  Val  Trp  Ala  Ala  Leu  Ala  Val  Gly  Leu  Glu  Leu  Trp  Ala  Ala
          35                        40                       45

GCG  CAC  GCC  TTG  CCC  GCC  CAG  GTG  GCA  TTT  ACA  CCC  TAC  GCC  CCG  GAG     192
Ala  His  Ala  Leu  Pro  Ala  Gln  Val  Ala  Phe  Thr  Pro  Tyr  Ala  Pro  Glu
     50                        55                       60

CCC  GGG  AGC  ACA  TGC  CGG  CTC  AGA  GAA  TAC  TAT  GAC  CAG  ACA  GCT  CAG     240
Pro  Gly  Ser  Thr  Cys  Arg  Leu  Arg  Glu  Tyr  Tyr  Asp  Gln  Thr  Ala  Gln
 65                       70                       75                      80

ATG  TGC  TGC  AGC  AAA  TGC  TCG  CCG  GGC  CAA  CAT  GCA  AAA  GTC  TTC  TGT     288
Met  Cys  Cys  Ser  Lys  Cys  Ser  Pro  Gly  Gln  His  Ala  Lys  Val  Phe  Cys
                    85                        90                       95

ACC  AAG  ACC  TCG  GAC  ACC  GTG  TGT  GAC  TCC  TGT  GAG  GAC  AGC  ACA  TAC     336
Thr  Lys  Thr  Ser  Asp  Thr  Val  Cys  Asp  Ser  Cys  Glu  Asp  Ser  Thr  Tyr
               100                      105                      110

ACC  CAG  CTC  TGG  AAC  TGG  GTT  CCC  GAG  TGC  TTG  AGC  TGT  GGC  TCC  CGC     384
Thr  Gln  Leu  Trp  Asn  Trp  Val  Pro  Glu  Cys  Leu  Ser  Cys  Gly  Ser  Arg
          115                      120                      125

TGT  AGC  TCT  GAC  CAG  GTG  GAA  ACT  CAA  GCC  TGC  ACT  CGG  GAA  CAG  AAC     432
Cys  Ser  Ser  Asp  Gln  Val  Glu  Thr  Gln  Ala  Cys  Thr  Arg  Glu  Gln  Asn
     130                      135                      140

CGC  ATC  TGC  ACC  TGC  AGG  CCC  GGC  TGG  TAC  TGC  GCG  CTG  AGC  AAG  CAG     480
Arg  Ile  Cys  Thr  Cys  Arg  Pro  Gly  Trp  Tyr  Cys  Ala  Leu  Ser  Lys  Gln
145                      150                      155                     160

GAG  GGG  TGC  CGG  CTG  TGC  GCG  CCG  CTG  CGC  AAG  TGC  CGC  CCG  GGC  TTC     528
Glu  Gly  Cys  Arg  Leu  Cys  Ala  Pro  Leu  Arg  Lys  Cys  Arg  Pro  Gly  Phe
                    165                      170                      175

GGC  GTG  GCC  AGA  CCA  GGA  ACT  GAA  ACA  TCA  GAC  GTG  GTG  TGC  AAG  CCC     576
Gly  Val  Ala  Arg  Pro  Gly  Thr  Glu  Thr  Ser  Asp  Val  Val  Cys  Lys  Pro
```

|     |     |     |     |     | 180 |     |     |     |     | 185 |     |     |     |     | 190 |     |     |      |
|-----|-----|-----|-----|-----|-----|-----|-----|-----|-----|-----|-----|-----|-----|-----|-----|-----|-----|------|
| TGT | GCC | CCG | GGG | ACG | TTC | TCC | AAC | ACG | ACT | TCA | TCC | ACG | GAT | ATT | TGC |     |     | 624  |
| Cys | Ala | Pro | Gly | Thr | Phe | Ser | Asn | Thr | Thr | Ser | Ser | Thr | Asp | Ile | Cys |     |     |      |
|     |     | 195 |     |     |     |     | 200 |     |     |     |     | 205 |     |     |     |     |     |      |

| AGG | CCC | CAC | CAG | ATC | TGT | AAC | GTG | GTG | GCC | ATC | CCT | GGG | AAT | GCA | AGC | 672 |
|-----|-----|-----|-----|-----|-----|-----|-----|-----|-----|-----|-----|-----|-----|-----|-----|-----|
| Arg | Pro | His | Gln | Ile | Cys | Asn | Val | Val | Ala | Ile | Pro | Gly | Asn | Ala | Ser |     |
|     | 210 |     |     |     |     | 215 |     |     |     |     | 220 |     |     |     |     |     |

| ATG | GAT | GCA | GTC | TGC | ACG | TCC | ACG | TCC | CCC | ACC | CGG | AGT | ATG | GCC | CCA | 720 |
|-----|-----|-----|-----|-----|-----|-----|-----|-----|-----|-----|-----|-----|-----|-----|-----|-----|
| Met | Asp | Ala | Val | Cys | Thr | Ser | Thr | Ser | Pro | Thr | Arg | Ser | Met | Ala | Pro |     |
| 225 |     |     |     |     | 230 |     |     |     |     | 235 |     |     |     |     | 240 |     |

| GGG | GCA | GTA | CAC | TTA | CCC | CAG | CCA | GTG | TCC | ACA | CGA | TCC | CAA | CAC | ACG | 768 |
|-----|-----|-----|-----|-----|-----|-----|-----|-----|-----|-----|-----|-----|-----|-----|-----|-----|
| Gly | Ala | Val | His | Leu | Pro | Gln | Pro | Val | Ser | Thr | Arg | Ser | Gln | His | Thr |     |
|     |     |     |     | 245 |     |     |     |     | 250 |     |     |     |     | 255 |     |     |

| CAG | CCA | ACT | CCA | GAA | CCC | AGC | ACT | GCT | CCA | AGC | ACC | TCC | TTC | CTG | CTC | 816 |
|-----|-----|-----|-----|-----|-----|-----|-----|-----|-----|-----|-----|-----|-----|-----|-----|-----|
| Gln | Pro | Thr | Pro | Glu | Pro | Ser | Thr | Ala | Pro | Ser | Thr | Ser | Phe | Leu | Leu |     |
|     |     |     | 260 |     |     |     |     | 265 |     |     |     |     | 270 |     |     |     |

| CCA | ATG | GGC | CCC | AGC | CCC | CCA | GCT | GAA | GGG | AGC | ACT | GGC | GAC | GAG | CCC | 864 |
|-----|-----|-----|-----|-----|-----|-----|-----|-----|-----|-----|-----|-----|-----|-----|-----|-----|
| Pro | Met | Gly | Pro | Ser | Pro | Pro | Ala | Glu | Gly | Ser | Thr | Gly | Asp | Glu | Pro |     |
|     |     | 275 |     |     |     |     | 280 |     |     |     |     | 285 |     |     |     |     |

| AAA | TCT | TGT | GAC | AAA | ACT | CAC | ACA | TGC | CCA | CCG | TGC | CCA | GCA | CCT | GAA | 912 |
|-----|-----|-----|-----|-----|-----|-----|-----|-----|-----|-----|-----|-----|-----|-----|-----|-----|
| Lys | Ser | Cys | Asp | Lys | Thr | His | Thr | Cys | Pro | Pro | Cys | Pro | Ala | Pro | Glu |     |
|     |     | 290 |     |     |     |     | 295 |     |     |     |     | 300 |     |     |     |     |

| CTC | CTG | GGG | GGA | CCG | TCA | GTC | TTC | CTC | TTC | CCC | CCA | AAA | CCC | AAG | GAC | 960 |
|-----|-----|-----|-----|-----|-----|-----|-----|-----|-----|-----|-----|-----|-----|-----|-----|-----|
| Leu | Leu | Gly | Gly | Pro | Ser | Val | Phe | Leu | Phe | Pro | Pro | Lys | Pro | Lys | Asp |     |
| 305 |     |     |     |     | 310 |     |     |     |     | 315 |     |     |     |     | 320 |     |

| ACC | CTC | ATG | ATC | TCC | CGG | ACC | CCT | GAG | GTC | ACA | TGC | GTG | GTG | GTG | GAC | 1008 |
|-----|-----|-----|-----|-----|-----|-----|-----|-----|-----|-----|-----|-----|-----|-----|-----|------|
| Thr | Leu | Met | Ile | Ser | Arg | Thr | Pro | Glu | Val | Thr | Cys | Val | Val | Val | Asp |      |
|     |     |     |     | 325 |     |     |     |     | 330 |     |     |     |     | 335 |     |      |

| GTG | AGC | CAC | GAA | GAC | CCT | GAG | GTC | AAG | TTC | AAC | TGG | TAC | GTG | GAC | GGC | 1056 |
|-----|-----|-----|-----|-----|-----|-----|-----|-----|-----|-----|-----|-----|-----|-----|-----|------|
| Val | Ser | His | Glu | Asp | Pro | Glu | Val | Lys | Phe | Asn | Trp | Tyr | Val | Asp | Gly |      |
|     |     |     | 340 |     |     |     |     | 345 |     |     |     |     | 350 |     |     |      |

| GTG | GAG | GTG | CAT | AAT | GCC | AAG | ACA | AAG | CCG | CGG | GAG | GAG | CAG | TAC | AAC | 1104 |
|-----|-----|-----|-----|-----|-----|-----|-----|-----|-----|-----|-----|-----|-----|-----|-----|------|
| Val | Glu | Val | His | Asn | Ala | Lys | Thr | Lys | Pro | Arg | Glu | Glu | Gln | Tyr | Asn |      |
|     |     |     | 355 |     |     |     |     | 360 |     |     |     |     | 365 |     |     |      |

| AGC | ACG | TAC | CGG | GTG | GTC | AGC | GTC | CTC | ACC | GTC | CTG | CAC | CAG | GAC | TGG | 1152 |
|-----|-----|-----|-----|-----|-----|-----|-----|-----|-----|-----|-----|-----|-----|-----|-----|------|
| Ser | Thr | Tyr | Arg | Val | Val | Ser | Val | Leu | Thr | Val | Leu | His | Gln | Asp | Trp |      |
|     | 370 |     |     |     |     | 375 |     |     |     |     | 380 |     |     |     |     |      |

| CTG | AAT | GGC | AAG | GAC | TAC | AAG | TGC | AAG | GTC | TCC | AAC | AAA | GCC | CTC | CCA | 1200 |
|-----|-----|-----|-----|-----|-----|-----|-----|-----|-----|-----|-----|-----|-----|-----|-----|------|
| Leu | Asn | Gly | Lys | Asp | Tyr | Lys | Cys | Lys | Val | Ser | Asn | Lys | Ala | Leu | Pro |      |
| 385 |     |     |     |     | 390 |     |     |     |     | 395 |     |     |     |     | 400 |      |

| GCC | CCC | ATG | CAG | AAA | ACC | ATC | TCC | AAA | GCC | AAA | GGG | CAG | CCC | CGA | GAA | 1248 |
|-----|-----|-----|-----|-----|-----|-----|-----|-----|-----|-----|-----|-----|-----|-----|-----|------|
| Ala | Pro | Met | Gln | Lys | Thr | Ile | Ser | Lys | Ala | Lys | Gly | Gln | Pro | Arg | Glu |      |
|     |     |     |     | 405 |     |     |     |     | 410 |     |     |     |     | 415 |     |      |

| CCA | CAG | GTG | TAC | ACC | CTG | CCC | CCA | TCC | CGG | GAT | GAG | CTG | ACC | AAG | AAC | 1296 |
|-----|-----|-----|-----|-----|-----|-----|-----|-----|-----|-----|-----|-----|-----|-----|-----|------|
| Pro | Gln | Val | Tyr | Thr | Leu | Pro | Pro | Ser | Arg | Asp | Glu | Leu | Thr | Lys | Asn |      |
|     |     |     | 420 |     |     |     |     | 425 |     |     |     |     | 430 |     |     |      |

| CAG | GTC | AGC | CTG | ACC | TGC | CTG | GTC | AAA | GGC | TTC | TAT | CCC | AGG | CAC | ATC | 1344 |
|-----|-----|-----|-----|-----|-----|-----|-----|-----|-----|-----|-----|-----|-----|-----|-----|------|
| Gln | Val | Ser | Leu | Thr | Cys | Leu | Val | Lys | Gly | Phe | Tyr | Pro | Arg | His | Ile |      |
|     |     | 435 |     |     |     |     | 440 |     |     |     |     | 445 |     |     |     |      |

| GCC | GTG | GAG | TGG | GAG | AGC | AAT | GGG | CAG | CCG | GAG | AAC | AAC | TAC | AAG | ACC | 1392 |
|-----|-----|-----|-----|-----|-----|-----|-----|-----|-----|-----|-----|-----|-----|-----|-----|------|
| Ala | Val | Glu | Trp | Glu | Ser | Asn | Gly | Gln | Pro | Glu | Asn | Asn | Tyr | Lys | Thr |      |
|     | 450 |     |     |     |     | 455 |     |     |     |     | 460 |     |     |     |     |      |

| ACG | CCT | CCC | GTG | CTG | GAC | TCC | GAC | GGC | TCC | TTC | TTC | CTC | TAC | AGC | AAG | 1440 |
|-----|-----|-----|-----|-----|-----|-----|-----|-----|-----|-----|-----|-----|-----|-----|-----|------|
| Thr | Pro | Pro | Val | Leu | Asp | Ser | Asp | Gly | Ser | Phe | Phe | Leu | Tyr | Ser | Lys |      |
| 465 |     |     |     | 470 |     |     |     |     | 475 |     |     |     |     |     | 480 |      |

| CTC | ACC | GTG | GAC | AAG | AGC | AGG | TGG | CAG | CAG | GGG | AAC | GTC | TTC | TCA | TGC | 1488 |
|-----|-----|-----|-----|-----|-----|-----|-----|-----|-----|-----|-----|-----|-----|-----|-----|------|
| Leu | Thr | Val | Asp | Lys | Ser | Arg | Trp | Gln | Gln | Gly | Asn | Val | Phe | Ser | Cys |      |
|     |     |     |     | 485 |     |     |     |     | 490 |     |     |     |     | 495 |     |      |

| TCC | GTG | ATG | CAT | GAG | GCT | CTG | CAC | AAC | CAC | TAC | ACG | CAG | AAG | AGC | CTC | 1536 |
|-----|-----|-----|-----|-----|-----|-----|-----|-----|-----|-----|-----|-----|-----|-----|-----|------|
| Ser | Val | Met | His | Glu | Ala | Leu | His | Asn | His | Tyr | Thr | Gln | Lys | Ser | Leu |      |

|     |     |     |     | 500 |     |     |     | 505 |     |     |     | 510 |     |     |     |      |
|-----|-----|-----|-----|-----|-----|-----|-----|-----|-----|-----|-----|-----|-----|-----|-----|------|
| TCC | CTG | TCT | CCG | GGT | AAA | TGA |     |     |     |     |     |     |     |     |     | 1557 |
| Ser | Leu | Ser | Pro | Gly | Lys |     |     |     |     |     |     |     |     |     |     |      |
|     |     | 515 |     |     |     |     |     |     |     |     |     |     |     |     |     |      |

( 2 ) INFORMATION FOR SEQ ID NO:4:

( i ) SEQUENCE CHARACTERISTICS:
        ( A ) LENGTH: 518 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Ala | Arg | Gln | Ala | Ala | Trp | Arg | Glu | Gly | Ala | Gly | Leu | Arg | Gly | Arg | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Ala | Arg | Ala | Gly | Gly | Asn | Arg | Thr | Pro | Pro | Ala | Ser | Met | Ala | Pro |
|     |     |     | 20  |     |     |     |     | 25  |     |     |     |     | 30  |     |     |
| Val | Ala | Val | Trp | Ala | Ala | Leu | Ala | Val | Gly | Leu | Glu | Leu | Trp | Ala | Ala |
|     |     |     | 35  |     |     |     | 40  |     |     |     |     | 45  |     |     |     |
| Ala | His | Ala | Leu | Pro | Ala | Gln | Val | Ala | Phe | Thr | Pro | Tyr | Ala | Pro | Glu |
|     | 50  |     |     |     |     | 55  |     |     |     |     | 60  |     |     |     |     |
| Pro | Gly | Ser | Thr | Cys | Arg | Leu | Arg | Glu | Tyr | Tyr | Asp | Gln | Thr | Ala | Gln |
| 65  |     |     |     |     | 70  |     |     |     |     | 75  |     |     |     |     | 80  |
| Met | Cys | Cys | Ser | Lys | Cys | Ser | Pro | Gly | Gln | His | Ala | Lys | Val | Phe | Cys |
|     |     |     |     | 85  |     |     |     |     | 90  |     |     |     |     | 95  |     |
| Thr | Lys | Thr | Ser | Asp | Thr | Val | Cys | Asp | Ser | Cys | Glu | Asp | Ser | Thr | Tyr |
|     |     |     | 100 |     |     |     |     | 105 |     |     |     |     | 110 |     |     |
| Thr | Gln | Leu | Trp | Asn | Trp | Val | Pro | Glu | Cys | Leu | Ser | Cys | Gly | Ser | Arg |
|     |     |     | 115 |     |     |     |     | 120 |     |     |     |     | 125 |     |     |
| Cys | Ser | Ser | Asp | Gln | Val | Glu | Thr | Gln | Ala | Cys | Thr | Arg | Glu | Gln | Asn |
|     | 130 |     |     |     |     | 135 |     |     |     |     | 140 |     |     |     |     |
| Arg | Ile | Cys | Thr | Cys | Arg | Pro | Gly | Trp | Tyr | Cys | Ala | Leu | Ser | Lys | Gln |
| 145 |     |     |     |     | 150 |     |     |     |     | 155 |     |     |     |     | 160 |
| Glu | Gly | Cys | Arg | Leu | Cys | Ala | Pro | Leu | Arg | Lys | Cys | Arg | Pro | Gly | Phe |
|     |     |     |     | 165 |     |     |     |     | 170 |     |     |     |     | 175 |     |
| Gly | Val | Ala | Arg | Pro | Gly | Thr | Glu | Thr | Ser | Asp | Val | Val | Cys | Lys | Pro |
|     |     |     | 180 |     |     |     |     | 185 |     |     |     |     | 190 |     |     |
| Cys | Ala | Pro | Gly | Thr | Phe | Ser | Asn | Thr | Thr | Ser | Ser | Thr | Asp | Ile | Cys |
|     |     |     | 195 |     |     |     |     | 200 |     |     |     |     | 205 |     |     |
| Arg | Pro | His | Gln | Ile | Cys | Asn | Val | Val | Ala | Ile | Pro | Gly | Asn | Ala | Ser |
|     | 210 |     |     |     |     | 215 |     |     |     |     | 220 |     |     |     |     |
| Met | Asp | Ala | Val | Cys | Thr | Ser | Thr | Ser | Pro | Thr | Arg | Ser | Met | Ala | Pro |
| 225 |     |     |     |     | 230 |     |     |     |     | 235 |     |     |     |     | 240 |
| Gly | Ala | Val | His | Leu | Pro | Gln | Pro | Val | Ser | Thr | Arg | Ser | Gln | His | Thr |
|     |     |     |     | 245 |     |     |     |     | 250 |     |     |     |     | 255 |     |
| Gln | Pro | Thr | Pro | Glu | Pro | Ser | Thr | Ala | Pro | Ser | Thr | Ser | Phe | Leu | Leu |
|     |     |     | 260 |     |     |     |     | 265 |     |     |     |     | 270 |     |     |
| Pro | Met | Gly | Pro | Ser | Pro | Pro | Ala | Glu | Gly | Ser | Thr | Gly | Asp | Glu | Pro |
|     |     | 275 |     |     |     |     | 280 |     |     |     |     | 285 |     |     |     |
| Lys | Ser | Cys | Asp | Lys | Thr | His | Thr | Cys | Pro | Pro | Cys | Pro | Ala | Pro | Glu |
|     | 290 |     |     |     |     | 295 |     |     |     |     | 300 |     |     |     |     |
| Leu | Leu | Gly | Gly | Pro | Ser | Val | Phe | Leu | Phe | Pro | Pro | Lys | Pro | Lys | Asp |
| 305 |     |     |     |     | 310 |     |     |     |     | 315 |     |     |     |     | 320 |
| Thr | Leu | Met | Ile | Ser | Arg | Thr | Pro | Glu | Val | Thr | Cys | Val | Val | Val | Asp |
|     |     |     |     | 325 |     |     |     |     | 330 |     |     |     |     | 335 |     |

| Val | Ser | His | Glu | Asp | Pro | Glu | Val | Lys | Phe | Asn | Trp | Tyr | Val | Asp | Gly |
| | | | 340 | | | | 345 | | | | | | 350 | | |
| Val | Glu | Val | His | Asn | Ala | Lys | Thr | Lys | Pro | Arg | Glu | Glu | Gln | Tyr | Asn |
| | | 355 | | | | 360 | | | | | | 365 | | | |
| Ser | Thr | Tyr | Arg | Val | Val | Ser | Val | Leu | Thr | Val | Leu | His | Gln | Asp | Trp |
| | 370 | | | | | 375 | | | | | 380 | | | | |
| Leu | Asn | Gly | Lys | Asp | Tyr | Lys | Cys | Lys | Val | Ser | Asn | Lys | Ala | Leu | Pro |
| 385 | | | | | 390 | | | | | 395 | | | | | 400 |
| Ala | Pro | Met | Gln | Lys | Thr | Ile | Ser | Lys | Ala | Lys | Gly | Gln | Pro | Arg | Glu |
| | | | | 405 | | | | | 410 | | | | | 415 | |
| Pro | Gln | Val | Tyr | Thr | Leu | Pro | Pro | Ser | Arg | Asp | Glu | Leu | Thr | Lys | Asn |
| | | | 420 | | | | | 425 | | | | | 430 | | |
| Gln | Val | Ser | Leu | Thr | Cys | Leu | Val | Lys | Gly | Phe | Tyr | Pro | Arg | His | Ile |
| | | 435 | | | | | 440 | | | | | 445 | | | |
| Ala | Val | Glu | Trp | Glu | Ser | Asn | Gly | Gln | Pro | Glu | Asn | Asn | Tyr | Lys | Thr |
| | 450 | | | | | 455 | | | | | 460 | | | | |
| Thr | Pro | Pro | Val | Leu | Asp | Ser | Asp | Gly | Ser | Phe | Phe | Leu | Tyr | Ser | Lys |
| 465 | | | | | 470 | | | | | 475 | | | | | 480 |
| Leu | Thr | Val | Asp | Lys | Ser | Arg | Trp | Gln | Gln | Gly | Asn | Val | Phe | Ser | Cys |
| | | | | 485 | | | | | 490 | | | | | 495 | |
| Ser | Val | Met | His | Glu | Ala | Leu | His | Asn | His | Tyr | Thr | Gln | Lys | Ser | Leu |
| | | | 500 | | | | | 505 | | | | | 510 | | |
| Ser | Leu | Ser | Pro | Gly | Lys |
| | | 515 | | | |

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i i ) IMMEDIATE SOURCE:
        ( B ) CLONE: oligonucleotide ( x i ) SEQUENCE DESCRIPTION: SEQ ID NO:5:

CGGTACGTGC TGTTGTTACT GC        22

METHODS OF LOWERING ACTIVE TNF-α LEVELS IN MAMMALS USING TUMOR NECROSIS FACTOR RECEPTOR

CROSS-REFERENCE TO RELATED APPLICATIONS

This is a continuation of application Ser. No. 07/946,236, filed Sep. 5, 1992, now abandoned, which is a continuation-in-part of U.S. application Ser. No. 523,635, filed May 10, 1990, now U.S. Pat. No. 5,345,760, which is a continuation-in-part of U.S. application Ser. No. 421,417, filed Oct. 13, 1989, now abandoned, which is a continuation-in-part of U.S. application Ser. No. 405,370, filed Sep. 11, 1989, now abandoned, which is a continuation-in-part of U.S. application Ser. No. 403,241, filed Sep. 5, 1989, now abandoned.

BACKGROUND OF THE INVENTION

The present invention relates generally to cytokine receptors and more specifically to a method of using tumor necrosis factor antagonists to suppress TNF-dependent inflammatory diseases.

Tumor necrosis factor-α(TNFα, also known as cachectin) and tumor necrosis factor-β (TNFβ, also known as lymphotoxin) are homologous mammalian endogenous secretory proteins capable of inducing a wide variety of effects on a large number of cell types. The great similarities in the structural and functional characteristics of these two cytokines have resulted in their collective description as "TNF." Complementary cDNA clones encoding TNFα (Pennica et al., *Nature* 312:724, 1984) and TNFβ (Gray et al., *Nature* 312:721, 1984) have been isolated, permitting further structural and biological characterization of TNF.

TNF proteins initiate their biological effect on cells by binding to specific TNF receptor (TNFR) proteins expressed on the plasma membrane of a TNF-responsive cell. Two distinct forms of TNFR are known to exist: Type I TNFR (TNFRI), having a molecular weight of approximately 75 kilodaltons, and Type II TNFR (TNFRII), having a molecular weight of approximately 55 kilodaltons. TNFRI and TNFRII each bind to both TNFα and TNFβ. TNFRI and TNFRII have both been molecularly cloned (Smith et al., *Science* 248:1019, 1990; Loetscher et al., *Cell* 61:351, 1990 and Schall et al., *Cell* 61:361, 1990), permitting recombinant expression and purification of soluble TNFR proteins.

Soluble TNF binding proteins from human urine have also been identified (Peetre et al., *Eur. J. Haematol.* 41:414, 1988; Seckinger et al., *J. Exp. Med.* 167:1511, 1988; Seckinger et al., *J. Biol. Chem.* 264:11966, 1989; UK Patent Application, Publ. No. 2 218 101 A to Seckinger et al.; Engelmann et al., *J. Biol. Chem.* 264:11974, 1989).

TNF antagonists, such as soluble TNFR and TNF binding proteins, bind to TNF and prevent TNF from binding to cell membrane bound TNF receptors. Such proteins may therefore be useful to suppress biological activities caused by TNF.

The role of TNF in mediated inflammatory diseases and the in vivo biological effects of such soluble TNFR and TNF binding protein proteins in suppressing such TNF-dependent inflammatory diseases have not been fully elucidated and potential therapeutic uses for TNF antagonists have yet to be identified.

SUMMARY OF THE INVENTION

The present invention provides a method of using TNF antagonists to suppress TNF-dependent inflammatory diseases. Specifically, the present invention provides a method of treating a human having arthritis comprising the step of administering a TNF antagonist, such as soluble human TNFR, to a human.

These and other aspects of the present invention will become evident upon reference to the following detailed description.

DETAILED DESCRIPTION OF THE INVENTION

Definitions

Figure 1:
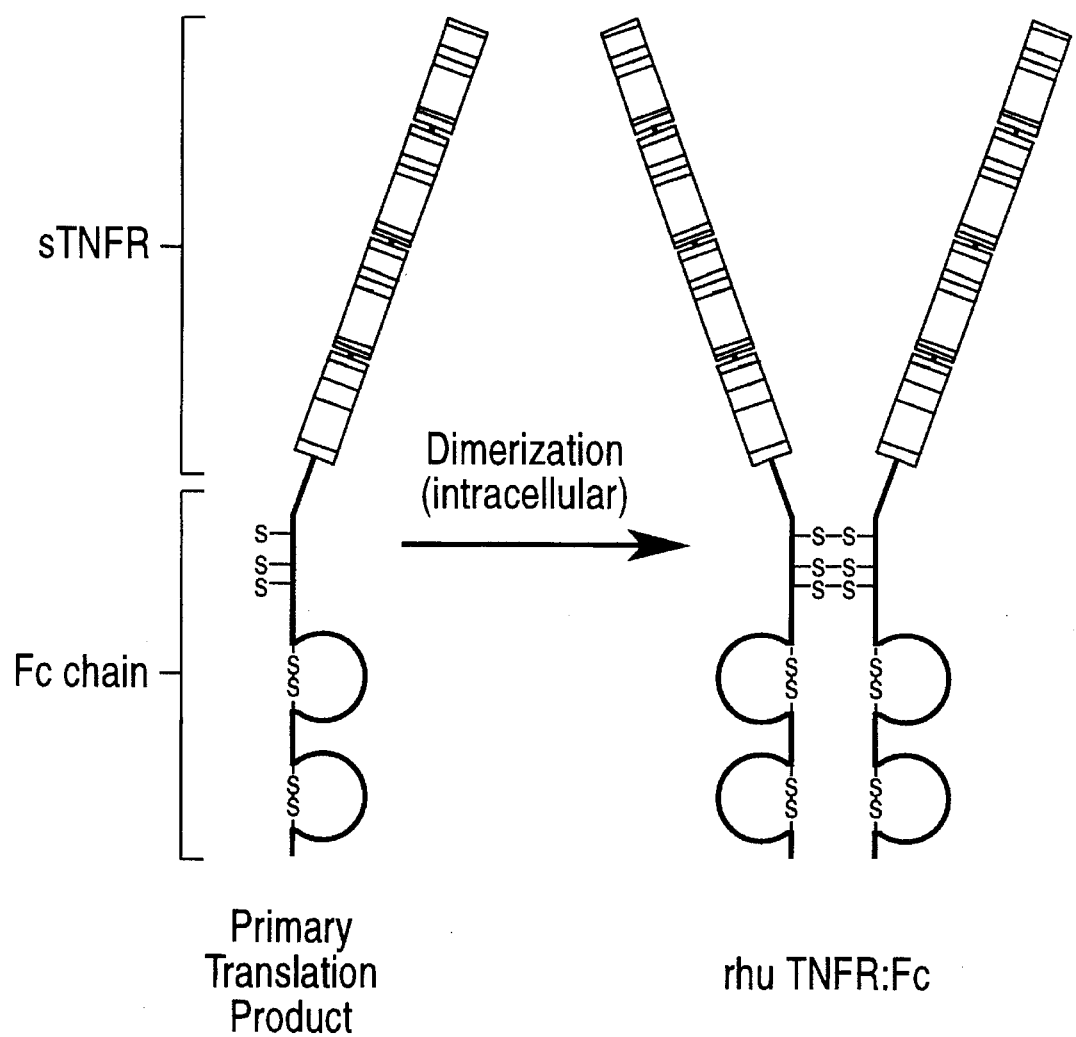
FIG. 1 shows the dimeric structure of the recombinant human TNFR/Fc fusion protein. The primary translation product of the plasmid coding for rhu TNFR/Fc is a single molecule of soluble TNFR linked to single chain of Fc derived from human IgG1. Following translation, but prior to secretion, this fusion molecule dimerizes via 3 cysteine residues in the Fc region to form dimeric rhu TNFR/Fc. Boxes denote structural domains of TNFR.

As used herein, the terms "TNF receptor" and "TNFR" refer to proteins having amino acid sequences which are substantially similar to the native mammalian TNF receptor or TNF binding protein amino acid sequences, and which are capable of binding TNF molecules and inhibiting TNF from binding to cell membrane bound TNFR. Two distinct types of TNFR are known to exist: Type I TNFR (TNFRI) and Type II TNFR (TNFRII). The mature full-length human TNFRI is a glycoprotein having a molecular weight of about 75–80 kilodaltons (kDa). The mature full-length human TNFRII is a glycoprotein having a molecular weight of about 55–60 kilodaltons (kDa). The preferred TNFRs of the present invention are soluble forms of TNFRI and TNFRII, as well as soluble TNF binding proteins. Soluble TNFR molecules include, for example, analogs or subunits of native proteins having at least 20 amino acids and which exhibit at least some biological activity in common with TNFRI, TNFRII or TNF binding proteins. Soluble TNFR constructs are devoid of a transmembrane region (and are secreted from the cell) but retain the ability to bind TNF. Various bioequivalent protein and amino acid analogs have an amino acid sequence corresponding to all or part of the extracellular region of a native TNFR, for example, huTNFRIΔ235, huTNFRIΔ185 and huTNFRIΔ163, or amino acid sequences substantially similar to the sequences of amino acids 1–163, amino acids 1–185, or amino acids 1–235 of SEQ ID NO:1, and which are biologically active in that they bind to TNF ligand. Equivalent soluble TNFRs include polypeptides which vary from these sequences by one or more substitutions, deletions, or additions, and which retain the ability to bind TNF or inhibit TNF signal transduction activity via cell surface bound TNF receptor proteins, for example huTNFRIΔx, wherein x is selected from the group consisting of any one of amino acids 163–235 of SEQ ID NO:1. Analogous deletions may be made to muTNFR. Inhibition of TNF signal transduction activity can be determined by transfecting cells with recombinant TNFR DNAs to obtain recombinant receptor expression. The cells are then contacted with TNF and the resulting metabolic effects examined. If an effect results which is attributable to the action of the ligand, then the recombinant receptor has signal transduction activity. Exemplary procedures for determining whether a polypeptide has signal transduction activity are disclosed by Idzerda et al., *J. Exp. Med.* 171:861 (1990); Curtis et al., *Proc. Natl. Acad. Sci. U.S.A.* 86:3045 (1989); Prywes et al., *EMBO J.* 5:2179 (1986) and Chou et al., *J. Biol. Chem.* 262:1842 (1987). Alternatively, primary cells or cell lines which express an endogenous TNF receptor and have a detectable biological response to TNF could also be utilized.

The nomenclature for TNFR analogs as used herein follows the convention of naming the protein (e.g., TNFR) preceded by either hu (for human) or mu (for murine) and followed by a Δ (to designate a deletion) and the number of the C-terminal amino acid. For example, huTNFRΔ235 refers to human TNFR having $Asp^{235}$ as the C-terminal amino acid (i.e., a polypeptide having the sequence of amino acids 1–235 of SEQ ID NO:1). In the absence of any human or murine species designation, TNFR refers generically to mammalian TNFR. Similarly, in the absence of any specific designation for deletion mutants, the term TNFR means all forms of TNFR, including routants and analogs which possess TNFR biological activity.

The term "isolated" or "purified", as used in the context of this specification to define the purity of TNFR protein or protein compositions, means that the protein or protein composition is substantially free of other proteins of natural or endogenous origin and contains less than about 1% by mass of protein contaminants residual of production processes. Such compositions, however, can contain other proteins added as stabilizers, carders, excipients or co-therapeutics. TNFR is isolated if it is detectable as a single protein band in a polyacrylamide gel by silver staining.

"Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein produced in a microbial expression system which is essentially free of native endogenous substances. Protein expressed in most bacterial cultures, e.g., *E. coli*, will be free of glycan. Protein expressed in yeast may have a glycosylation pattern different from that expressed in mammalian cells.

"Biologically active," as used throughout the specification as a characteristic of TNF receptors, means that a particular molecule shares sufficient amino acid sequence similarity with the embodiments of the present invention disclosed herein to be capable of binding detectable quantities of TNF, transmitting a TNF stimulus to a cell, for example, as a component of a hybrid receptor construct, or cross-reacting with anti-TNFR antibodies raised against TNFR from natural (i.e., nonrecombinant) sources. Preferably, biologically active TNF receptors within the scope of the present invention are capable of binding greater than 0.1 nmoles TNF per nmole receptor, and most preferably, greater than 0.5 nmole TNF per nmole receptor in standard binding assays (see below).

Soluble TNF Antagonists and Analogs

The present invention utilizes isolated and purified TNF antagonist polypeptides. The isolated and purified TNF antagonist polypeptides used in this invention are substantially free of other contaminating materials of natural or endogenous origin and contain less than about 1% by mass of protein contaminants residual of production processes. The TNF antagonist polypeptides used in this invention are optionally without associated native-pattern glycosylation.

In preferred aspects of the present invention, the TNF antagonists are selected from the group consisting of soluble human TNFRI and TNFR II. The pCAV/NOT-TNFR vector, containing the human TNFRI cDNA clone 1, was used to express and purify soluble human TNFRI. pCAV/NOT-TNFR has been deposited with the American Type Culture Collection, 12301 Parklawn Drive, Rockville, Md. 20852, U.S.A. (Accession No. 68088) under the name pCAV/NOT-TNFR.

Like most mammalian genes, mammalian TNF receptors are presumably encoded by multi-exon genes. Alternative mRNA constructs which can be attributed to different mRNA splicing events following transcription, and which share large regions of identity or similarity with the cDNAs claimed herein may also be used.

Other mammalian TNFR cDNAs may be isolated by using an appropriate human TNFR DNA sequence as a probe for screening a particular mammalian cDNA library by cross-species hybridization. Mammalian TNFR used in the present invention includes, by way of example, primate, human, murine, canine, feline, bovine, ovine, equine and porcine TNFR. Mammalian TNFRs can be obtained by cross species hybridization, using a single stranded cDNA derived from the human TNFR DNA sequence as a hybridization probe to isolate TNFR cDNAs from mammalian cDNA libraries.

Derivatives of TNFR which may be used in the present invention also include various structural forms of the primary protein which retain biological activity. Due to the presence of ionizable amino and carboxyl groups, for example, a TNFR protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to TNFR amino acid side chains or at the N- or C-termini. Other derivatives of TNFR include covalent or aggregative conjugates of TNFR or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader). TNFR protein fusions can comprise peptides added to facilitate purification or identification of TNFR (e.g., poly-His). The amino acid sequence of TNF receptor can also be linked to the peptide Asp-Tyr-Lys-Asp-Asp-Asp-Asp-Lys (DYKDDDDK) (Hopp et al., Bio/Technology 6:1204,1988.) The latter sequence is highly antigenic and provides an epitope reversibly bound by a specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in E. coli.

TNFR with or without associated native-pattern glycosylation may also be used. TNFR expressed in yeast or mammalian expression systems, e.g., COS-7 cells, may be similar or slightly different in molecular weight and glycosylation pattern than the native molecules, depending upon the expression system. Expression of TNFR DNAs in bacteria such as E. coli provides non-glycosylated molecules. Functional mutant analogs of mammalian TNFR having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, Asn provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

TNFR derivatives may also be obtained by mutations of TNFR or its subunits. A TNFR mutant, as referred to herein, is a polypeptide homologous to TNFR but which has an amino acid sequence different from native TNFR because of a deletion, insertion or substitution.

Bioequivalent analogs of TNFR proteins may be constructed by, for example, making various substitutions of residues or sequences or deleting terminal or internal residues or sequences not needed for biological activity. For example, cysteine residues can be deleted (e.g., $Cys^{178}$) or replaced with other amino acids to prevent formation of unnecessary or incorrect intramolecular disulfide bridges upon renaturation. Other approaches to mutagenesis involve modification of adjacent dibasic amino acid residues to enhance expression in yeast systems in which KEX2 protease activity is present. Generally, substitutions should be made conservatively; i.e., the most preferred substitute amino acids are those having physiochemical characteristics resembling those of the residue to be replaced. Similarly, when a deletion or insertion strategy is adopted, the potential effect of the deletion or insertion on biological activity should be considered. Substantially similar polypeptide sequences, as defined above, generally comprise a like number of amino acids sequences, although C-terminal truncations for the purpose of constructing soluble TNFRs will contain fewer amino acid sequences. In order to preserve the biological activity of TNFRs, deletions and substitutions will preferably result in homologous or conservatively substituted sequences, meaning that a given residue is replaced by a biologically similar residue. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Moreover, particular amino acid differences between human, murine and other mammalian TNFRs is suggestive of additional conservative substitutions that may be made without altering the essential biological characteristics of TNFR.

Subunits of TNFR may be constructed by deleting terminal or internal residues or sequences. Particularly preferred sequences include those in which the transmembrane region and intracellular domain of TNFR are deleted or substituted with hydrophilic residues to facilitate secretion of the receptor into the cell culture medium. The resulting protein is referred to as a soluble TNFR molecule which retains its ability to bind TNF. A particularly preferred soluble TNFR construct is TNFRIΔ235 (the sequence of amino acids 1–235 of SEQ ID NO:1), which comprises the entire extracellular region of TNFRI, terminating with $Asp^{235}$ immediately adjacent the transmembrane region. Additional amino acids may be deleted from the transmembrane region while retaining TNF binding activity. For example, huTNFRIΔ183 which comprises the sequence of amino acids 1–183 of SEQ ID NO: 1, and TNFRIΔ163 which comprises the sequence of amino acids 1–163 of SEQ ID NO: 1, retain the ability to bind TNF ligand. TNFRIΔ142, however, does not retain the ability to bind TNF ligand. This suggests that one or both of $Cys^{157}$ and $Cys^{163}$ is required for formation of an intramolecular disulfide bridge for the proper folding of TNFRI. $Cys^{178}$, which was deleted without any apparent adverse effect on the ability of the soluble TNFRI to bind TNF, does not appear to be essential for proper folding of TNFRI. Thus, any deletion C-terminal to $Cys^{163}$ would be expected to result in a biologically active soluble TNFRI. The present invention contemplates use of such soluble TNFR constructs corresponding to all or part of the extracellular region of TNFR terminating with any amino acid after $Cys^{163}$. Other C-terminal deletions, such as TNFRIΔ157, may be made as a matter of convenience by cutting TNFR cDNA with appropriate restriction enzymes and, if necessary, reconstructing specific sequences with synthetic oligonucleotide linkers. Soluble TNFR with N-terminal deletions may also be used in the present invention. For example, the N-terminus of TNFRI may begin with $Leu^1$, $Pro^2$ or $Ala^3$ without significantly affecting the ability of TNFRI to effectively act as a TNF antagonist. The resulting soluble TNFR constructs are then inserted and expressed in appropriate expression vectors and assayed for the ability to bind TNF.

Mutations in nucleotide sequences constructed for expression of analog TNFR must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed TNFR mutants screened for the desired activity.

Not all mutations in the nucleotide sequence which encodes TNFR will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known E. coli preference codons for E. coli expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques, Jan.* 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Both monovalent forms and polyvalent forms of TNFR may also be used in the present invention. Polyvalent forms possess multiple TNFR binding sites for TNF ligand. For example, a bivalent soluble TNFR may consist of two tandem repeats of amino acids 1–235 of SEQ ID NO:1, separated by a linker region. Alternate polyvalent forms may also be constructed, for example, by chemically coupling TNFR to any clinically acceptable carder molecule, a polymer selected from the group consisting of Ficoll, polyethylene glycol or dextran using conventional coupling techniques. Alternatively, TNFR may be chemically coupled to biotin, and the biotin-TNFR conjugate then allowed to bind to avidin, resulting in tetravalent avidin/biotin/TNFR molecules. TNFR may also be covalently coupled to dinitrophenol (DNP) or trinitrophenol (TNP) and the resulting conjugate precipitated with anti-DNP or anti-TNP-IgM, to form decameric conjugates with a valency of 10 for TNFR binding sites.

A recombinant chimeric antibody molecule may also be produced having TNFR sequences substituted for the variable domains of either or both of the immunoglobulin molecule heavy and light chains and having unmodified constant region domains. For example, chimeric TNFR/IgG$_1$ may be produced from two chimeric genes—a TNFR/human κ light chain chimera (TNFR/G$_\kappa$) and a TNFR/human γ$_1$ heavy chain chimera (TNFR/C$_{\gamma-1}$). Following transcription and translation of the two chimeric genes, the gene products assemble into a single chimeric antibody molecule having TNFR displayed bivalently. Such polyvalent forms of TNFR may have enhanced binding affinity for TNF ligand. One specific example of a TNFR/Fc fusion protein is disclosed in SEQ ID NO:3 and SEQ ID NO:4. Additional details relating to the construction of such chimeric antibody molecules are disclosed in WO 89/09622 and EP 315062.

Expression of Recombinant TNFR

Recombinant expression vectors are preferably used to amplify or express DNA encoding TNFR to obtain purified TNFR. Recombinant expression vectors are replicable DNA constructs which have synthetic or cDNA-derived DNA fragments encoding mammalian TNFR or bioequivalent analogs operably linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements may include an operator sequence to control transcription, a sequence encoding suitable mRNA ribosomal binding sites. The ability to replicate in a host, usually conferred by an origin of replication, and a selection gene to facilitate recognition of transformants may additionally be incorporated. DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

DNA sequences encoding mammalian TNF receptors which are to be expressed in a microorganism will preferably contain no introns that could prematurely terminate transcription of DNA into mRNA; however, premature termination of transcription may be desirable, for example, where it would result in mutants having advantageous C-terminal truncations, for example, deletion of a transmembrane region to yield a soluble receptor not bound to the cell membrane. Due to code degeneracy, there can be considerable variation in nucleotide sequences encoding the same amino acid sequence. Other embodiments include sequences capable of hybridizing to the sequences of the provided cDNA under moderately stringent conditions (50° C., 2× SSC) and other sequences hybridizing or degenerate to those which encode biologically active TNF receptor polypeptides.

Recombinant TNFR DNA is expressed or amplified in a recombinant expression system comprising a substantially homogeneous monoculture of suitable host microorganisms, for example, bacteria such as *E. coli* or yeast such as *S. cerevisiae*, which have stably integrated (by transformation or transfection) a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

Transformed host cells are cells which have been transformed or transfected with TNFR vectors constructed using recombinant DNA techniques. Transformed host cells ordinarily express TNFR, but host cells transformed for purposes of cloning or amplifying TNFR DNA do not need to express TNFR. Expressed TNFR will be deposited in the cell membrane or secreted into the culture supernatant, depending on the TNFR DNA selected. Suitable host cells for expression of mammalian TNFR include prokaryotes, yeast or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed to produce mammalian TNFR using RNAs derived from the DNA constructs of the present invention. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotic expression hosts may be used for expression of TNFR that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphyolococcus, although others may also be employed as a matter of choice.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis. U.S.A.). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage $\lambda$ $P_L$ promoter and cI857ts thermolabile repressor. Plasmid vectors available from the American Type Culture Collection which incorporate derivatives of the $\lambda$ $P_L$ promoter include plasmid pHUB2, resident in *E. coli*. strain JMB9 (ATCC 37092) and pPLc28, resident in *E. coli*. RR1 (ATCC 53082).

Recombinant TNFR proteins may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2µ yeast plasmid or an autonomously replicating sequence (ARS), promoter, DNA encoding TNFR, sequences for polyadenylation and transcription termination and a selection gene. Preferably, yeast vectors will include an origin of replication and selectable marker permitting transformation of both yeast and *E. coli*., e.g., the ampicillin resistance gene of *E. coli*. and *S. cerevisiae* TRP1 or URA3 gene, which provides a selection marker for a mutant strain of yeast lacking the ability to grow in tryptophan, and a promoter derived from a highly expressed yeast gene to induce transcription of a structural sequence downstream. The presence of the TRP1 or URA3 lesion in the yeast host cell genome then provides an effective environment for detecting transformation by growth in the absence of tryptophan or uracil.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 7:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pUC18 for selection and replication in *E. coli*. ($Amp^r$ gene and origin of replication) and yeast DNA sequences including a glucose-repressible ADH2 promoter and a-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. U.S.A.* 81:5330, 1984. The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. U.S.A.* 75:1929, 1978, selecting for $Trp^+$ transformants in a selective medium consisting of 0.67% yeast nitrogen base, 0.5% casamino acids, 2% glucose, 10 µg/ml adenine and 20 µg/ml uracil or URA+ tranformants in medium consisting of 0.67% YNB, with amino acids and bases as described by Sherman et al., *Laboratory Course Manual for Methods in Yeast Genetics*, Cold Spring Harbor Laboratory, Cold Spring Harbor, N.Y., 1986.

Host strains transformed by vectors comprising the ADH2 promoter may be grown for expression in a rich medium consisting of 1% yeast extract, 2% peptone, and 1% or 4% glucose supplemented with 80 µg/ml adenine and 80 µg/ml uracil. Derepression of the ADH2 promoter occurs upon exhaustion of medium glucose. Crude yeast supernatants are harvested by filtration and held at 4° C. prior to further purification.

Various mammalian or insect cell culture systems are also advantageously employed to express recombinant protein. Expression of recombinant proteins in mammalian cells is particularly preferred because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind 3 site toward the Bgl1 site located in the vital origin of replication is included. Further, mammalian genomic TNFR promoter, control and/or signal sequences may be utilized, provided such control sequences are compatible with the host cell chosen. Additional details regarding the use of a mammalian high expression vector to produce a recombinant mammalian TNF receptor are provided in Examples 2 and 7 below. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986).

Recombinant expression vectors comprising TNFR cDNAs are stably integrated into a host cell's DNA. Elevated levels of expression product is achieved by selecting for cell lines having amplified numbers of vector DNA. Cell lines having amplified numbers of vector DNA are selected, for example, by transforming a host cell with a vector comprising a DNA sequence which encodes an enzyme which is inhibited by a known drug. The vector may also comprise a DNA sequence which encodes a desired protein. Alternatively, the host cell may be co-transformed with a second vector which comprises the DNA sequence which encodes the desired protein. The transformed or co-transformed host cells are then cultured in increasing concentrations of the known drug, thereby selecting for drug-resistant cells. Such drug-resistant cells survive in increased concentrations of the toxic drug by over-production of the enzyme which is inhibited by the drug, frequently as a result of amplification of the gene encoding the enzyme. Where drug resistance is caused by an increase in the copy number of the vector DNA encoding the inhibitable enzyme, there is a concomitant co-amplification of the vector DNA encoding the desired protein (TNFR) in the host cell's DNA.

A preferred system for such co-amplification uses the gene for dihydrofolate reductase (DHFR), which can be inhibited by the drug methotrexate (MTX). To achieve co-amplification, a host cell which lacks an active gene encoding DHFR is either transformed with a vector which comprises DNA sequence encoding DHFR and a desired protein, or is co-transformed with a vector comprising a DNA sequence encoding DHFR and a vector comprising a DNA sequence encoding the desired protein. The transformed or co-transformed host cells are cultured in media containing increasing levels of MTX, and those cells lines which survive are selected.

A particularly preferred co-amplification system uses the gene for glutamine synthetase (GS), which is responsible for the synthesis of glutamate and ammonia using the hydrolysis of ATP to ADP to drive the reaction. GS is subject to inhibition by a variety of inhibitors, for example methionine sulphoximine (MSX). Thus, TNFR can be expressed in high concentrations by co-amplifying cells transformed with a vector comprising the DNA sequence for GS and a desired protein, or co-transformed with a vector comprising a DNA sequence encoding GS and a vector comprising a DNA sequence encoding the desired protein, culturing the host cells in media containing increasing levels of MSX and selecting for surviving cells. The GS co-amplification system, appropriate recombinant expression vectors and cells lines, are described in the following PCT applications: WO 87/04462, WO 89/01036, WO 89/10404 and WO 86/05807.

Recombinant proteins are preferably expressed by co-amplification of DHFR or GS in a mammalian host cell, such as Chinese Hamster Ovary (CHO) cells, or alternatively in a murine myeloma cell line, such as SP2/0-Ag14 or NS0 or a rat myeloma cell line, such as YB2/3.0-Ag20, disclosed in PCT applications WO/89/10404 and WO 86/05807.

A preferred eukaryotic vector for expression of TNFR DNA is disclosed below in Example 1. This vector, referred to as pCAV/NOT, was derived from the mammalian high expression vector pDC201 and contains regulatory sequences from SV40, adenovirus-2, and human cytomegalovirus.

Purification of Recombinant TNFR

Purified mammalian TNF receptors or analogs are prepared by culturing suitable host/vector systems to express the recombinant translation products of the DNAs of the present invention, which are then purified from culture media or cell extracts.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. For example, a suitable affinity matrix can comprise a TNF or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred.

Finally, one or more reversed-phase high performance liquid chromatography (RP-HPLC) steps employing hydrophobic RP-HPLC media, e.g., silica gel having pendant methyl or other aliphatic groups, can be employed to further purify a TNFR composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant mammalian TNFR can be disrupted by any convenient method, including freeze-thaw cycling, sonication, mechanical disruption, or use of cell lysing agents.

Fermentation of yeast which express mammalian TNFR as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Human TNFR synthesized in recombinant culture is characterized by the presence of non-human cell components, including proteins, in amounts and of a character which depend upon the purification steps taken to recover human TNFR from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of TNFR free of proteins which may be normally associated with TNFR as it is found in nature in its species of origin, e.g. in cells, cell exudates or body fluids.

Therapeutic Administration of Recombinant Soluble TNFR

The present invention provides methods of suppressing TNF-dependent inflammatory responses in humans comprising administering an effective amount of a TNF antagonist, such as TNFR, and a suitable diluent and carrier.

For therapeutic use, purified soluble TNFR protein is administered to a patient, preferably a human, for treatment of arthritis. Thus, for example, soluble TNFR protein compositions can be administered, for example, via intra-articular, intraperitoneal or subcutaneous routes by bolus injection, continuous infusion, sustained release from implants, or other suitable techniques. Typically, a soluble TNFR therapeutic agent will be administered in the form of a composition comprising purified protein in conjunction with physiologically acceptable carriers, excipients or diluents. Such carriers will be nontoxic to recipients at the dosages and concentrations employed. Ordinarily, the preparation of such compositions entails combining the TNFR with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. In accordance with appropriate industry standards, preservatives may also be added, such as benzyl alcohol. The amount and frequency of administration will depend, of course, on such factors as the nature and severity of the indication being treated, the desired response, the condition of the patient, and so forth.

TNF antagonist proteins are administered to a mammal, preferably a human, for the purpose treating TNF-dependent inflammatory diseases, such as arthritis. For example, TNFRI proteins inhibit TNF-dependent arthritic responses. Because of the primary roles IL-1 and IL-2 play in the production of TNF, combination therapy using TNFR in combination with IL-1R and/or IL-2R may be preferred in the treatment of TNF-associated clinical indications. In the treatment of humans, soluble human TNFR is preferred. Either Type I IL-1R or Type II IL-1R, or a combination thereof, may be used in accordance with the present invention to treat TNF-dependent inflammatory diseases, such as arthritis. Other types of TNF binding proteins may be similarly used.

For treatment of arthritis, TNFR is administered in systemic amounts ranging from about 0.1 mg/kg/week to about 100 mg/kg/week. In preferred embodiments of the present invention, TNFR is administered in amounts ranging from about 0.5 mg/kg/week to about 50 mg/kg/week. For local intra-articular administration, dosages preferably range from about 0.01 mg/kg to about 1.0 mg/kg per injection.

The following examples are offered by way of illustration, and not by way of limitation.

EXAMPLES

Example 1

Expression and Purification Of Soluble Human TNFRI

The cloning of the cDNA for the 80 kD form of the human TNF receptor has been described in detail (Smith et al., *Science* 248:1019, 1990). The expression vector pCAV/NOT-TNFR (ATCC 68088) containing the TNFR cDNA clone 1 was used to prepare and express a soluble human TNFRI as follows.

A cDNA encoding a soluble human TNFRIΔ235 (the primary translation product of which had the sequence of amino acids -22-235 of SEQ ID NO:1) was constructed by excising an 840 bp fragment from pCAV/NOT-TNFR with the restriction enzymes Not1 and Pvu2. Not1 cuts at the multiple cloning site of pCAV/NOT-TNFR and Pvu2 cuts within the TNFR coding region 20 nucleotides 5' of the transmembrane region. In order to reconstruct the 3' end of the TNFR sequences, two oligonucleotides were synthesized and annealed to create the following oligonucleotide linker encoding amino acids corresponding to amino acids 229–235 of SEQ ID NO:1:

```
Pvu2                              BamH1  Bgl2
CTGAAGGGAGCACTGGCGACTAAGGATCCA

GACTTCCCTCGTGACCGCTGATTCCTAGGTCTAG
AlaGluGlySerThrGlyAspEnd
```

This oligonucleotide linker has terminal Pvu2 and Bgl2 restriction sites, regenerates 20 nucleotides of the TNFR, followed by a termination codon (underlined) and a BamH1 restriction site (for convenience in isolating the entire soluble TNFR by Not1/BamH1 digestion). This oligonucleotide was then ligated with the 840 bp Not1/Pvu2 TNFR insert into Bgl2/Not1 cut pCAV/NOT to yield psolhuTNFRΔ235/CAVNOT, which was transfected into COS-7 cells as described above. The host cells expressed a mature a soluble human TNFRI protein having the sequence of amino acids 1-235 which was capable of binding TNF.

Example 2

Construction and Expression of Soluble Human TNFR/Fc Fusion Protein

A schematic diagram showing the construction of a recombinant soluble human TNFR:Fc expression vector is shown in FIG. 1. The rhu TNFR:Fc fusion gene was created by ligating the following fragments into Bluescript®, a commercially available cloning vector (Stratagene):

1) An 867 bp Asp718-Pvu2 fragment from pCAV/NOT-TNFR (ATCC 68088) containing the cDNA encoding the truncated TNFR.

2) A 700 bp Sty1-Spe1 fragment from plasmid pIXY498 coding for 232 amino acids of the Fc portion of human IgG1. Plasmid pIXY498 is a yeast expression vector containing the Fc fragment of human IgG1 (see FIG. 2).

3) An oligonucleotide linker, to fuse the truncated TNFR with the human IgG1 Fc fragment. This linker was created by PCR (polymerase chain reaction) amplification using two primers, one having the sequence CCCCAGCTGAAGGGAGCACTGGCG ACGAGCCAAATCTTGTGACAAAACTC (nucleotides 833–883 of SEQ ID NO:3) which encodes the 3' end of the truncated TNF receptor and the 5' end of human IgG1, and the other having the sequence CGGTACGTGCTGTTGTTACTGC (SEQ ID NO:5), an antisense sequence encoding nucleotides 257–237 of human IgG1. The template for this reaction was pIXY498. The reaction product was digested with Pvu2 and Sty1, and a 115 bp fragment was isolated.

Figure 2:
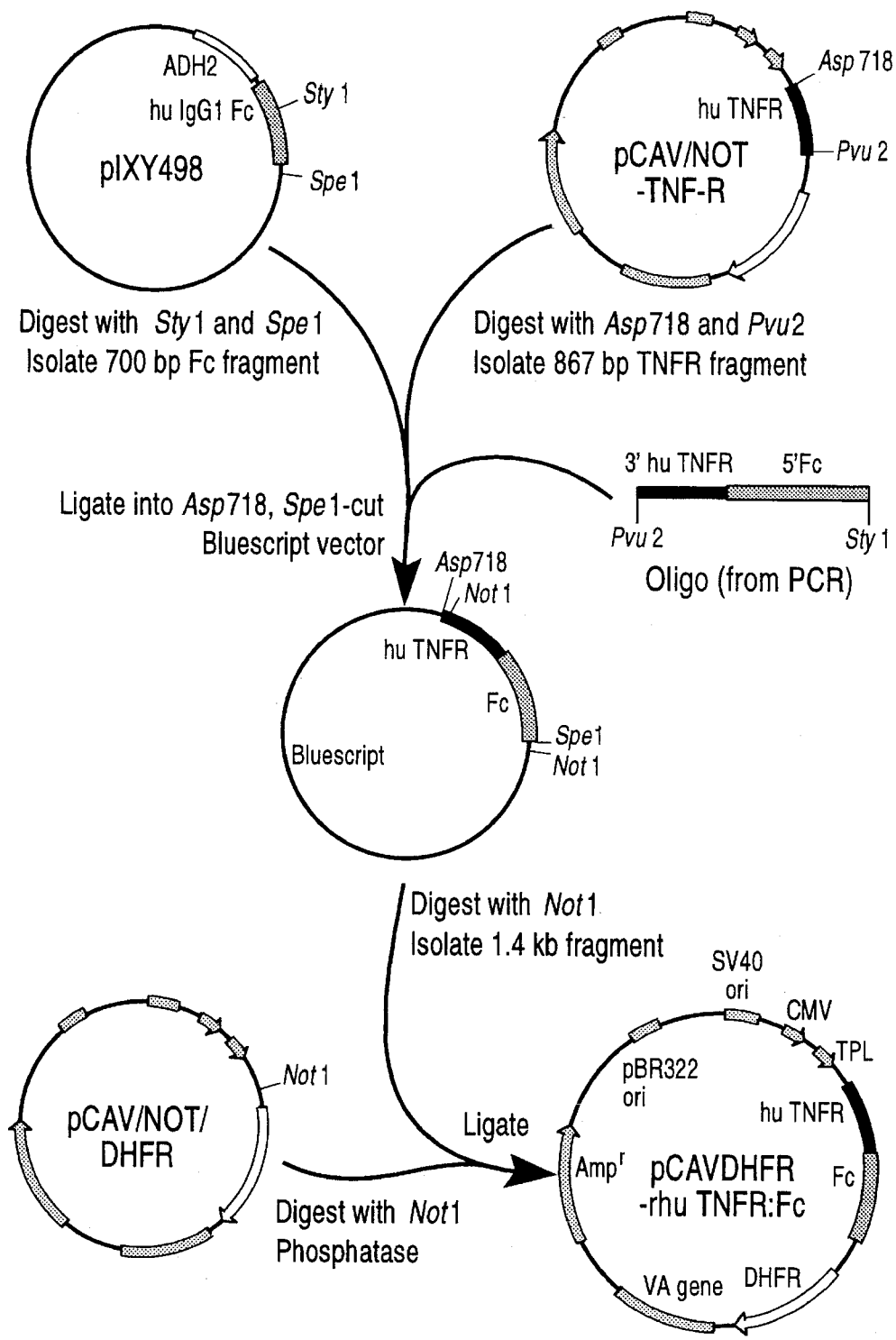
FIG. 2 shows the construction of plasmid pCAVDHFR rhu TNFR/Fc. Abbreviations are as follows: ADH2, yeast alcohol dehydrogenase gene and regulatory region; CMV, cytomegalovirus immediate early enhancer; TPL, adenovirus-2 tripartite leader; VA, adenovirus-2 virus-associated RNA genes I and II; DHFR, hamster dihydrofolate reductase gene.

This construct was then digested with Not1 and the resulting 1.4 kilobase fragment containing the rhu TNFR:Fc fusion DNA sequence was ligated into the Not1 site of plasmid CAV/NOT/DHFR. Plasmid pCAV/NOT/DHFR was derived from plasmid pCAV/NOT by inserting the hamster dihydrofolate reductase DNA sequence (DHFR) into the Hpa1 site of pCAV/NOT (FIG. 2). This construct was designated plasmid pCAVDHFRhuTNFRFc. The entire coding region sequence was confirmed by DNA sequencing and is depicted in FIG. 2.

To prepare the host strain, DXB-11 CHO cells deficient in the expression of dihydrofolate reductase (DHFR) were obtained from Dr. Lawren Chasin at Columbia University. A bank of 100 vials of these cells was established, and representative vials were sent to Microbiological Associates for examination via the following procedures:

| Test | Result |
|---|---|
| 1. Transmission Electron Microscopy (TEM) | Type A only, |
| 2. Sterility - Bacterial and Fungal | negative |
| 3. Mycoplasma | negative |
| 4. Mouse Antibody Production (MAP) | negative |

All transfections and amplification steps were performed in a separate laboratory set aside for this purpose. Only mycoplasma-free cell lines were allowed into this facility.

Transfections were performed by mixing pCAVDHFRhuTNFRFc plasmid DNA with Lipofectin™ reagent from Gibco BRL. Approximately 10>g of DNA was added to 10 cm petri dishes containing CHO DXB-11 cells. After the initial transfection, cells were selected for the expression of DHFR by subculturing in selective medium lacking glycine, hypoxanthine and thymidine. The resulting colonies were then transferred to 24 well plates and analyzed for rhu TNFR:Fc expression. The highest expressing cultures were subjected to amplification by exposure to increasing concentrations of methotrexate (MTX). Cells able to grow at 25 nM MTX were cloned by limiting dilution in 96 well plates. The highest expressing clones were transferred to suspension culture and the final selection of clone 4-4FC102A5-3 was made based on its high level of rhu TNFR:Fc expression under these conditions.

Example 3

Expression of Monomeric Soluble TNF Receptors in CHO Cells

Soluble TNF receptor was expressed in Chinese Hamster Ovary (CHO) cells using the glutamine-synthetase (GS) gene amplification system, substantially as described in PCT patent application Nos. WO87/04462 and WO89/01036. Briefly, CHO cells are transfected with an expression vector containing genes for both TNFR and GS. CHO cells are selected for GS gene expression based on the ability of the transfected DNA to confer resistance to low levels of methionine sulphoximine (MSX). GS sequence amplification events in such cells are selected using elevated MSX concentrations. In this way, contiguous TNFR sequences are also amplified and enhanced TNFR expression is achieved.

The vector used in the GS expression system was psolTNFR/P6/PSVLGS, which was constructed as follows. First, the vector pSVLGS.1 (described in PCT Application Nos. WO87/04462 and WO89/01036, and available from Celltech, Ltd., Berkshire, UK) was cut with the BamH1 restriction enzyme and dephosphorylated with calf intestinal alkaline phosphatase (CIAP) to prevent the vector from religating to itself. The BamH1 cut pSVLGS.1 fragment was then ligated to a 2.4 kb BamH1 to Bgl2 fragment of pEE6hCMV (described in PCT Application No. WO89/01036, also available from Celltech) which was cut with Bgl2, BamH1 and Fsp1 to avoid two fragments of similar size, to yield an 11.2 kb vector designated p6/PSVLGS.1. pSVLGS.1 contains the glutamine synthetase selectable marker gene under control of the SV40 later promoter. The BamH1 to Bgl2 fragment of pEE6hCMV contains the human cytomegalovirus major immediate early promoter (hCMV), a polylinker, and the SV40 early polyadenylation signal. The coding sequences for soluble TNFR were added to p6/PSVLGS.1 by excising a Not1 to BamH1 fragment from the expression vector psolTNFR/CAVNOT (made according to Example 3 above), blunt ending with Klenow and ligating with SmaI cut dephosphorylated p6/PSVLGS.1, thereby placing the solTNFR coding sequences under the control of the hCMV promoter. This resulted in a single plasmid vector in which the SV40/GS and hCMB/solTNFR transcription units are transcribed in opposite directions. This vector was designated psolTNFR/P6/PSVLGS.

psolTNFR/P6/PSVLGS was used to transfect CHO-K1 cells (available from ATCC, Rochville, Md., under accession number CCL 61) as follows. A monolayer of CHO-K1 cells were grown to subconfluency in Minimum Essential Medium (MEM) 10× (Gibco: 330-1581AJ) without glutamine and supplemented with 10% dialysed fetal bovine serum (Gibco: 220-6300AJ), 1 mM sodium pyruvate (Sigma), MEM non-essential amino acids (Gibco: 320-1140AG), 500 µM asparagine and glutamate (Sigma) and nucleosides (30 µM adenosine, guanosine, cytidine and uridine and 10 µM thymidine)(Sigma).

Approximately 1×10$^6$ cells per 10 cm petri dish were transfected with 10 ug of psolTNFR/P6/PSVLGS by standard calcium phosphate precipitation, substantially as described by Graham & van der Eb, Virology 52:456 (1983). Cells were subjected to glycerol shock (15% glycerol in serum-free culture medium for approximately 1.5 minutes) approximately 4 hours after transfection, substantially as described by Frost & Williams, Virology 91:39 (1978), and then washed with serum-free medium. One day later, transfected cells were fed with fresh selective medium containing MSX at a final concentration of 25 uM. Colonies of MSX-resistant surviving cells were visible within 3–4 weeks. Surviving colonies were transferred to 24-well plates and allowed to grow to confluency in selective medium. Conditioned medium from confluent wells were then assayed for soluble TNFR activity using standard binding assays. These assays indicated that the colonies expressed biologically active soluble TNFR.

In order to select for GS gene amplification, several MSX-resistant cell lines are transfected with psolTNFR/P6/PSVLGS and grown in various concentrations of MSX. For each cell line, approximately 1×10$^6$ cells are plated in gradually increasing concentrations of 100 uM, 250 uM, 500 uM and 1 mM MSX and incubated for 10–14 days. After 12 days, colonies resistant to the higher levels of MSX appear. The surviving colonies are assayed for TNFR activity. Each of these highly resistant cell lines contains cells which arise from multiple independent amplification events. From these cells lines, one or more of the most highly resistant cells lines are isolated. The amplified cells with high production rates are then cloned by limiting dilution cloning. Mass cell cultures of the transfectants secrete active soluble TNFR.

Example 4

Effect of Soluble TNFR on Antigen-Induced Arthritis in Rats

Lewis rats previously immunized with methylated bovine serum albumin (mBSA) in complete Freund's adjuvant develop antigen-induced arthritis (AIA) when challenged with mBSA in knee joints. Administration of rhu TNFR:Fc, TNFR monomer, recombinant murine soluble IL-1 receptor (rm IL-1R) or a combination of TNFR monomer plus rm IL-1R was shown to be effective in suppressing the effects of antigen-induced arthritis in rats.

Lewis rats were immunized in the hind flank with 0.5 mg mBSA in complete Freund's adjuvant. Twenty-one days later (day 0), the animals were injected in both hind knee joints with 50 μg mBSA in pyrogen-free saline. Groups of six rats were injected intra-articularly in both knee joints on that day and on the following 2 days (days 0, 1 and 2) as indicated below in Table A:

TABLE A

| Treatment and Dosage Schedule | | |
|---|---|---|
| Group | Treatment | Dose |
| 1 | rhu TNFR/Fc | 10 μg |
| 2 | rhu TNFR/Fc | 5 μg |
| 3 | rmu IL-1 Receptor | 1 μg |
| 4 | TNFR Monomer | 5 μg |
| 5 | TNFR Monomer/rmu IL-1R | 10 μg/1 μg |
| 6 | Diluent (saline) | — |

Knee joint width was measured daily on days 0–6 relative to treatment. TNFR monomer was produced in CHO cells according to Example 2. The rhu TNFR:Fc used in this experiment was produced in BHK (hamster kidney) cells. This material is similar to the CHO cell-derived TNFR.

Figure 3:
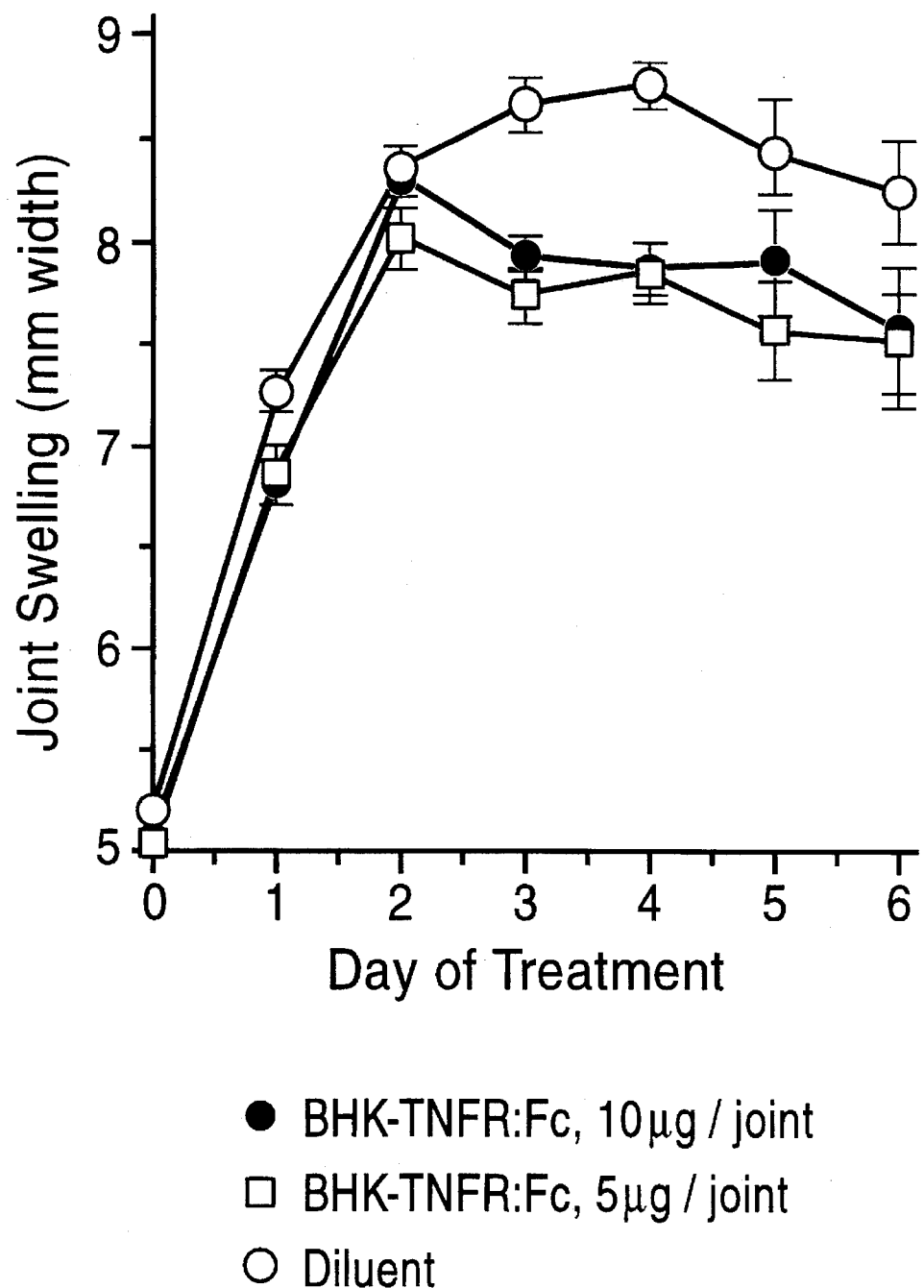
FIGS. 3 and 4 are graphs showing the effect of intra-articular administration of recombinant human TNFR/Fc, monomeric TNFR, recombinant murine IL-1R and TNFR monomer combined with rmuIL-1R on antigen-induced arthritis in rats. The data indicate that TNFR/Fc, TNFR monomer, rmu IL-1R and TNFR combined with IL-1R suppress inflammation associated with antigen-induced arthritis.
Figure 4:
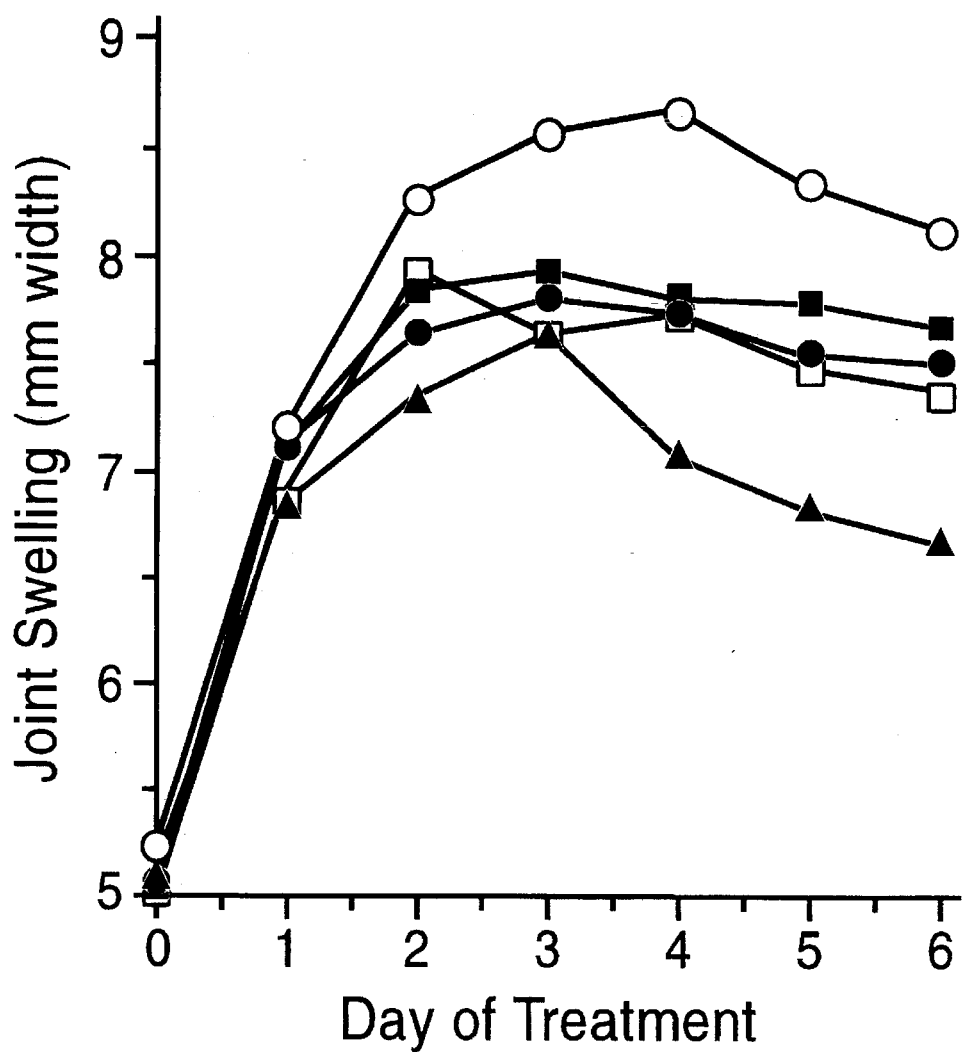

FIGS. 3 and 4 demonstrate that treatment with BHK-derived rhu TNFR:Fc at the time of mBSA challenge and for two days following challenge resulted in a reduction of knee-joint swelling in comparison to diluent-treated control rats. A reduction in joint swelling and inflammation was observed in rats treated with 5 or 10 μg BHK-derived rhu TNFR:Fc or 5 μg TNFR monomer or 1 μg of rmuIL-1R. Reduction in joint swelling was even more pronounced when rmuIL-1R and TNFR monomer treatment was combined.

Histopathological examination of the joints harvested on day 6 was performed to confirm the degree of swelling. Histopathology scores were derived by evaluating knee joints and scoring their condition as follows: Grade 1, minimal, <10% of area affected; Grade 2, moderate, 10–50% of area affected; Grade 3, marked, at least 50%, but less than all, of area affected; Grade 4, maximal, total area severely affected. A variety of lesions/alterations involving five knee joint structures were evaluated: joint capsule, joint space, synovial membrane, articular cartilage, and subchondral bone. Each structural alteration was scored from 1 to 4, and the scores were added and means were calculated. Histopathology results are expressed as the mean score in each treatment group.

The following Table B shows histopathology results, which also indicate that rhu TNFR:Fc, TNFR monomer and rmu IL-1R were effective in reducing the severity of antigen-induced arthritis, and that a combination of rm IL-1R and TNFR monomer was more effective than either receptor alone.

TABLE B

Effect of rhu TNFR:Fc on Antigen Induced Arthritis in Rats

| Treatment | Histopathology Score (Mean ± SD (SE)) | Number of Animals |
|---|---|---|
| Saline | 18.4 ± 4.9 (1.5) | 10 |
| 1.0 μg rmu IL-1R | 13.1 ± 4.7 (1.7) | 8 |
| 10.0 μg TNFR monomer | 12.8 ± 3.1 (1.1) | 8 |
| 1.0 μg rmu IL-1R/10.0 μg TNFR monomer | 7.9 ± 5.2 (2.0) | 5 |
| 5.0 μg TNFR monomer | 13.4 ± 2.8 (1.0) | 9 |
| 5.0 μg rhu TNFR:Fc (BHK) | 13.4 ± 3.6 (1.3) | 8 |

In summary, treatment with rhu TNFR/Fc, TNFR monomer, or rmu IL-1R at the time of mBSA challenge and for two days following challenge resulted in a reduction of knee-joint swelling in comparison to diluent-treated control rats. A combination of both rmu IL-1R and TNFR monomer resulted in greater reduction of swelling than either receptor molecule alone. Histopathology results also indicated that rhu TNFR/Fc, TNFR and rmu IL-1R were effective in reducing the severity of antigen-induced arthritis, and that a combination of rmu IL-1R and TNFR monomer was more effective than either receptor alone.

Example 5

Effect of Soluble TNFR on Collagen-Induced Arthritis in B 10.RIII Mice

B10.RIII mice previously immunized with porcine type II collagen (CII) in complete Freund's adjuvant consistently develop collagen-induced arthritis (CIA). Administration of rhu TNFR:Fc was shown to be effective in suppressing the symptoms of CIA in mice.

B10.RIII mice were immunized intradermally with 100 μg porcine type II collagen (CII) in complete Freund's adjuvant to induced arthritic symptoms. Approximately 14–17 days post-immunization, symptoms of clinical arthritis began to appear in the mice, with 90–100% of the mice displaying severe arthritis by day 28. Mice were injected intraperitoneally with TNFR/Fc or PBS to determine the effect of soluble TNFR/Fc on CIA. Mice were assessed for symptoms of arthritis at 12 weeks post-immunization.

Figure 5:
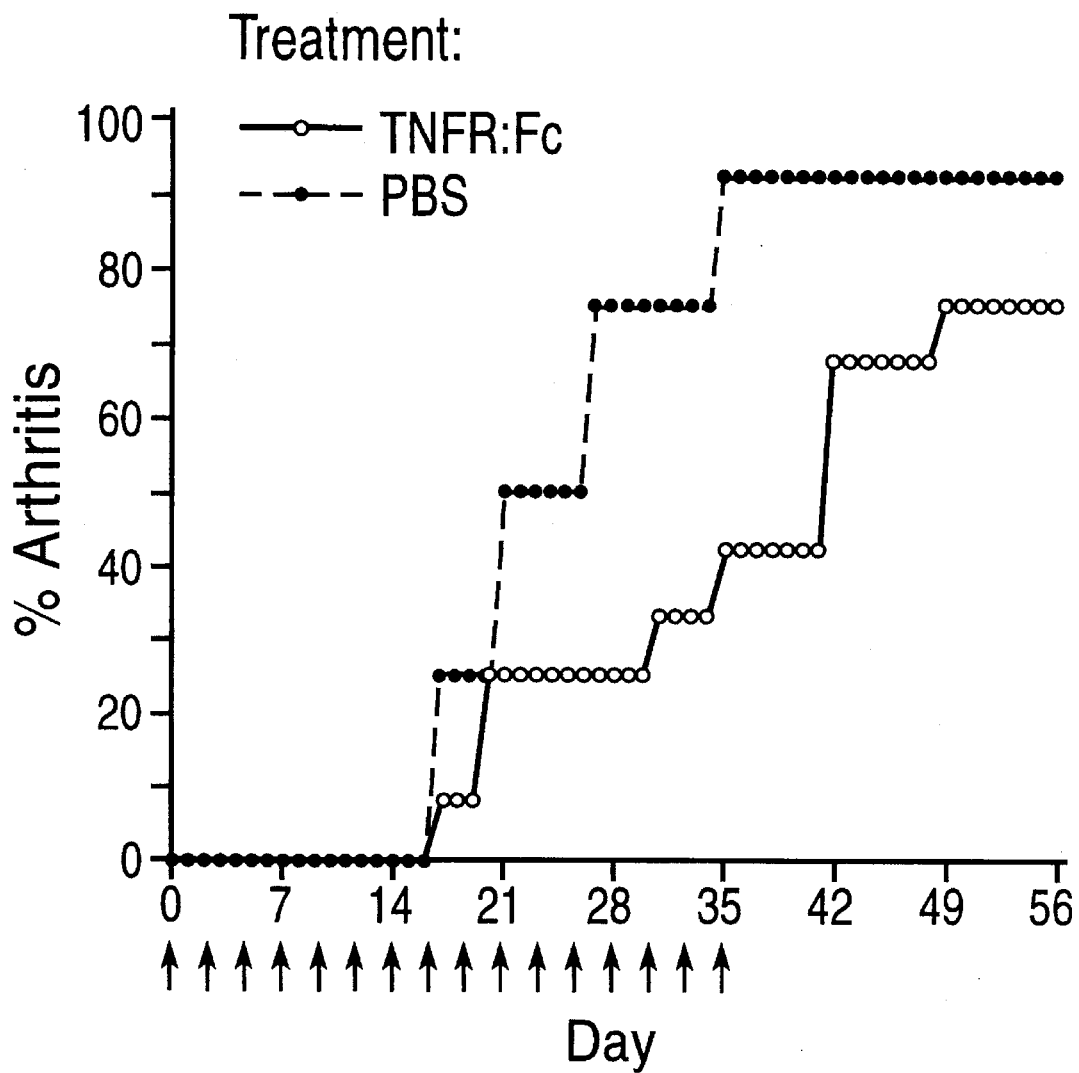
FIG. 5 shows the effect of intraperitoneal administration of recombinant human TNFR/Fc and PBS (vehicle control) on the development of collagen induced arthritis (CIA) in B 10.RIII mice. TNFR/Fc significantly delayed the onset of CIA.

In a first experiment, TNFR/Fc was administered over the entire period of CIA development. Twelve mice were injected with 10 μg TNFR/Fc, 3 days per week, from days 0 to 35. Twelve control mice were injected with PBS. FIG. 5 shows that TNFR/Fc significantly reduced the incidence of arthritis when compared to controls. Upon cessation of treatment with TNFR/Fc, the mice developed arthritis.

In a second experiment, TNFR/Fc was administered during only the developmental stages of CIA on days −1–17 relative to immunization, as set forth in the following Table C.

TABLE C

Effect of rhu TNFR:Fc Administered During Inductive Stage of CIA

| Treatment | Incidence (Positive/Total) | Onset (Mean Day ± SE) | Severity (Mean ± SE) |
|---|---|---|---|
| 30 μg TNFR/Fc Days −1, 3 | 10/10 | 24 ± 2 | 10.5 ± 0.5 |
| 10 μg TNFR/Fc Days −1 to 17 (alternate days) | 8/10 | 21 ± 2 | 8.6 ± 0.6 |
| 100 μl PBS Days −1 to 17 (alternate days) | 10/10 | 18 ± 1 | 10.6 ± 0.4 |

These data show that TNFR/Fc delayed the onset of arthritis, but that CIA was unaltered in mice receiving 30 μg TNFR/Fc the day before and 3 days after immunization with type II collagen. Mice given 10 μg TNFR/Fc, every other day, from day −1 to day 17 displayed a slight decrease in CIA incidence and severity versus controls injected with PBS.

In a third experiment, TNFR/Fc was administered during only the progressive stages of CIA every other day on days 14–28 post-immunization as set forth in the following Table D.

TABLE D

Effect of rhu TNFR:Fc Administered During Progressive Stage of CIA

| Treatment | Incidence (Positive/Total) | Onset (Mean Day ± SE) | Severity (Mean ± SE) |
|---|---|---|---|
| 10 μg TNFR/Fc Days 14–28 (alternate days) | 8/9 | 27 ± 6 | 8.6 ± 1.3 |
| 100 μl PBS Days 14–28 (alternate days) | 9/9 | 21 ± 1 | 8.7 ± 0.6 |

These data show that mice given 10 μg TNFR/Fc, every other day, from days 14–28 showed a slight delay in CIA onset when compared to control animals. However, the incidence and severity of arthritis appears to be unaltered.

In summary, these experiments indicate that TNFR/Fc was effective in delaying the onset of CIA when administered over the entire course of CIA development.

Example 6

Effect of Soluble TNFR on Collagen-Induced Arthritis in DBA/1 Mice

The effect of soluble TNFR/Fc on CIA in DBA/1 mice previously immunized with porcine type II collagen (CII) in complete Freund's adjuvant was also tested. Administration of rhu TNFR:Fc was shown to be effective in suppressing the symptoms of CIA.

In this experiment, DBA/1 mice were immunized with 100 μg of CII and then injected intraperitoneally with 50 μg recombinant soluble human TNFR/Fc in sterile saline from day 21 to day 28. Control mice received sterile saline (vehicle) injections. This treatment period was prior to the development of the clinical signs of CIA, but during the development of DTH responses to type II collagen and rapid IgG anti-CII production.

Figure 6:
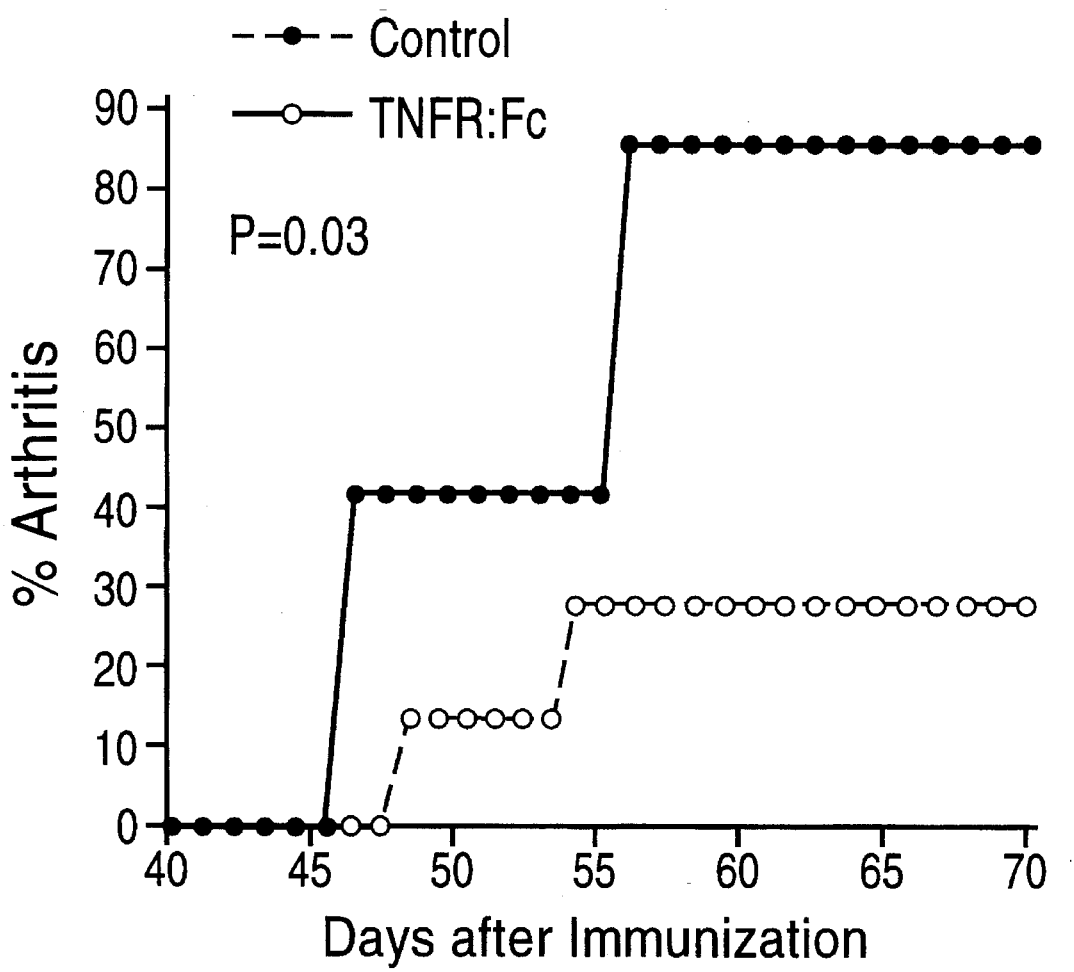
FIG. 6 shows the effect of intraperitoneal administration of recombinant human TNFR/Fc and PBS (vehicle control) on the development of collagen induced arthritis (CIA) in DBA/1 mice. TNFR/Fc significantly delayed the onset of CIA.
Figure 7:
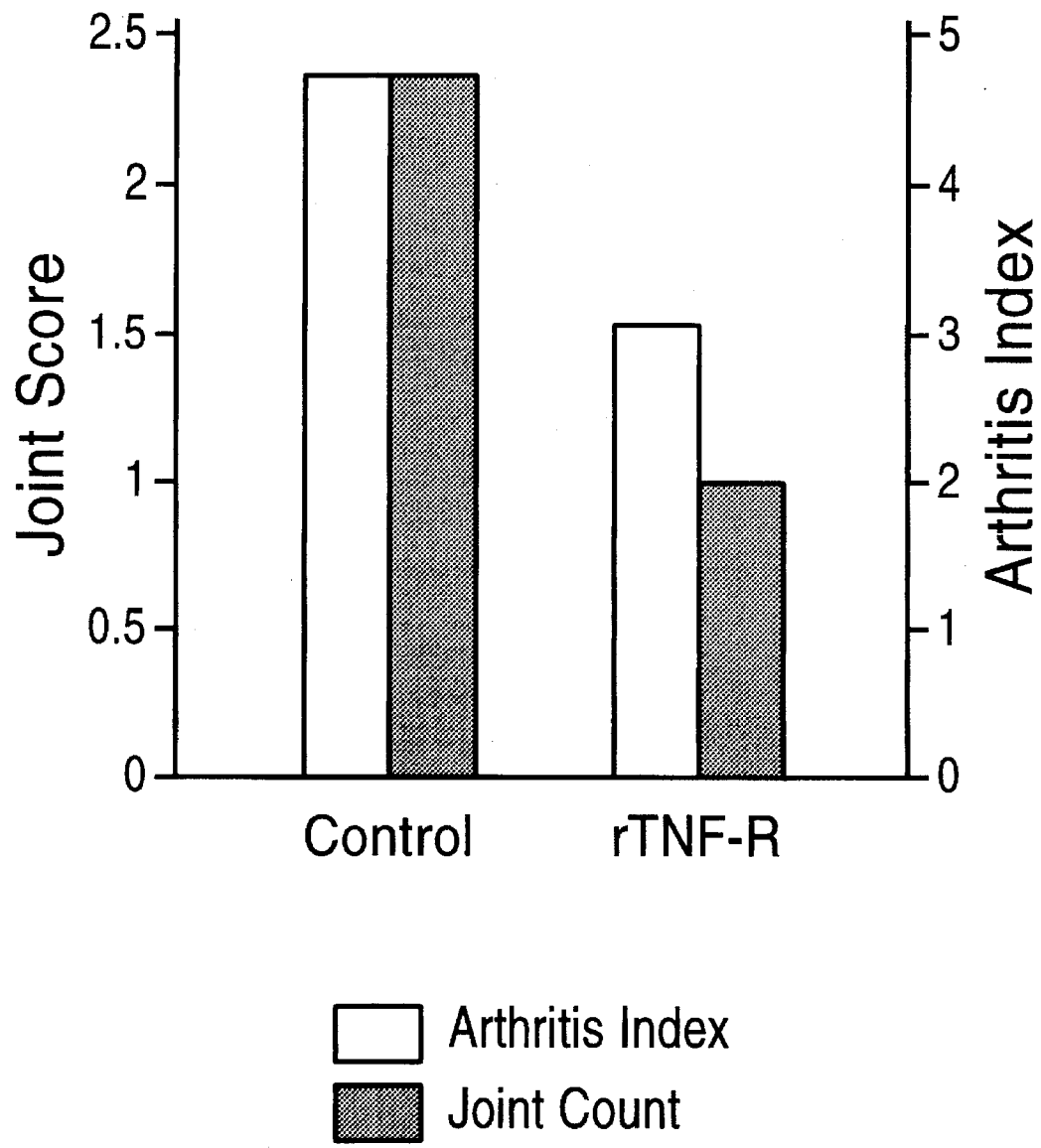
FIG. 7 shows that administration of TNFR/Fc in mice reduced the arthritis index and the number of joints showing signs of arthritis.

Both groups of mice were assessed for the development of CIA for 70 days, and onset of CIA for 44–55 days post-immunization. FIGS. 6 and 7 show that TNFR/Fc significantly reduced the incidence of CIA compared with controls (28% vs. 86%; $p<0.03$), and reduced both arthritis index (a subjective measure of severity) and the number of involved joints. The antibody response to CII was significantly lower immediately post treatment with TNFR/Fc (day 28), but antibody levels were equivalent at the conclusion of the experiment (day 70).

These results indicate that TNFR/Fc is effective in reducing the incidence of CIA in mice and may therefore be useful in the treatment arthritis.

We claim:

1. A method for lowering the levels of active TNF-α in a mammal in need thereof which comprises administering to said mammal a TNF-lowering amount of a TNF antagonist selected from the group consisting of:
   (a) a TNF receptor comprising the sequence of amino acids 3–163 of SEQ ID NO:1; and
   (b) a chimeric antibody comprising a TNF receptor according to (a) fused to the constant domain of an immunoglobulin molecule.

2. A method for lowering the levels of active TNF-α in a mammal in need thereof which comprises administering to said mammal a TNF-lowering amount of a TNF receptor comprising the sequence of amino acids 3–163 of SEQ ID NO:1.

3. A method for lowering the levels of active TNF-α in a mammal in need thereof which comprises administering to said mammal a TNF-lowering amount of a chimeric antibody comprising a TNF receptor comprising the sequence of amino acids 3–163 of SEQ ID NO:1 fused to the constant domain of an immunoglobulin molecule.

4. A method for lowering the levels of active TNF-α in a mammal having arthritis, which comprises administering to such mammal a therapeutically effective amount of a TNF-antagonist selected from the group consisting of:
   (a) a TNF receptor comprising the sequence of amino acids 3–163 of SEQ ID NO:1; and
   (b) a chimeric antibody comprising a TNF receptor according to (a) fused to the constant domain of an immunogloblin molecule.

5. A method for lowering the levels of active TNF-α in a mammal having arthritis, which comprises administering to said mammal a TNF-lowering amount of a TNF receptor comprising the sequence of amino acids 3–163 of SEQ ID NO:1.

6. A method for lowering the levels of active TNF-α in a mammal having arthritis, which comprises administering to said mammal a TNF-lowering amount of a chimeric antibody comprising a TNF receptor comprising the sequence of amino acids 3–163 of SEQ ID NO:1 fused to the constant domain of an immunoglobulin molecule.

* * * * *